US011138485B2

(12) United States Patent
Sugar et al.

(10) Patent No.: US 11,138,485 B2
(45) Date of Patent: Oct. 5, 2021

(54) USAGE, CONDITION AND LOCATION TAG AND SYSTEM

(71) Applicant: Emanate Wireless, Inc., Ijamsville, MD (US)

(72) Inventors: Gary L. Sugar, Shaker Heights, OH (US); Neil R. Diener, Hudson, OH (US); Yohannes Tesfai, Silver Spring, MD (US); Chandra Vaidyanathan, Rockville, MD (US)

(73) Assignee: EMANATE WIRELESS, INC., Ijamsville, MD (US)

( * ) Notice: Subject to any disclaimer, the term of this patent is extended or adjusted under 35 U.S.C. 154(b) by 54 days.

(21) Appl. No.: 16/663,447

(22) Filed: Oct. 25, 2019

(65) Prior Publication Data
US 2020/0143216 A1     May 7, 2020

Related U.S. Application Data

(60) Provisional application No. 62/753,964, filed on Nov. 1, 2018.

(51) Int. Cl.
| G06K 19/07 | (2006.01) |
| G06K 7/00 | (2006.01) |
| G06K 7/10 | (2006.01) |
| G06K 19/077 | (2006.01) |
| G06K 19/073 | (2006.01) |

(52) U.S. Cl.
CPC ....... *G06K 19/0723* (2013.01); *G06K 7/0008* (2013.01); *G06K 7/10366* (2013.01); *G06K 19/0702* (2013.01); *G06K 19/0716* (2013.01); *G06K 19/07354* (2013.01); *G06K 19/07758* (2013.01)

(58) Field of Classification Search
CPC ............. G06K 19/0723; G06K 7/0008; G06K 7/10366; G06K 19/0702; G06K 19/0716; G06K 19/07354; G06K 19/07758
See application file for complete search history.

(56) References Cited

U.S. PATENT DOCUMENTS

| 3,976,985 A | 8/1976 | Schalow et al. |
| 4,325,223 A | 4/1982 | Cantley |
| 4,502,287 A | 3/1985 | Hare et al. |
| 5,402,112 A | 3/1995 | Thompson |
| 5,473,244 A | 12/1995 | Libove et al. |
| 5,729,129 A * | 3/1998 | Acker ...................... A61B 5/06 324/207.12 |
| 5,969,516 A | 10/1999 | Wottrich |

(Continued)

FOREIGN PATENT DOCUMENTS

| JP | 2007093469 A | 4/2007 |
| JP | 2012027628 A | 2/2012 |

*Primary Examiner* — Thomas D Alunkal
(74) *Attorney, Agent, or Firm* — Edell, Shapiro & Finnan, LLC

(57) ABSTRACT

A Usage, Condition and Location System (UCLS) tag is provided, which is an active RFID tag that, in addition to location, is configured to determine the usage state and operating condition of a device. The UCLS tag includes sensors that measure physical activity of the associated equipment (vibration, magnetic activity, temperature, etc.). Algorithms may use the information obtained from the UCLS tags to map the measured sensor data to a contextual usage state and operating condition of the device.

25 Claims, 27 Drawing Sheets

(56) References Cited

U.S. PATENT DOCUMENTS

| | | | |
|---|---|---|---|
| 6,275,681 B1 | 8/2001 | Vega et al. | |
| 7,135,974 B2 | 11/2006 | Hernandez et al. | |
| 7,962,130 B2 | 6/2011 | Moorer et al. | |
| 7,964,989 B1 | 6/2011 | Puschnigg et al. | |
| 8,334,771 B2 | 12/2012 | Matsuyama et al. | |
| 8,442,792 B1 | 5/2013 | Elberbaum | |
| 8,725,455 B2 | 5/2014 | Kriss | |
| 9,020,769 B2 | 4/2015 | Rada et al. | |
| 9,431,839 B2 | 8/2016 | Suomela | |
| 9,679,235 B2 | 6/2017 | Sugar | |
| 10,126,334 B2 | 11/2018 | Sugar | |
| 10,240,861 B2 * | 3/2019 | Sugar | G08B 21/182 |
| 2003/0007470 A1 | 1/2003 | Grilli et al. | |
| 2003/0197613 A1 | 10/2003 | Hernandez et al. | |
| 2005/0136972 A1 | 6/2005 | Smith et al. | |
| 2005/0237192 A1 | 10/2005 | Krieger | |
| 2006/0047538 A1 * | 3/2006 | Condurso | G16H 70/40 705/3 |
| 2006/0113987 A1 | 6/2006 | Sorensen | |
| 2006/0190538 A1 | 8/2006 | Hwang et al. | |
| 2006/0193393 A1 | 8/2006 | Shen et al. | |
| 2006/0218415 A1 | 9/2006 | Mak-Fan et al. | |
| 2007/0015549 A1 | 1/2007 | Hernandez et al. | |
| 2007/0029384 A1 | 2/2007 | Atherton | |
| 2007/0103296 A1 * | 5/2007 | Paessel | A01K 27/009 340/539.22 |
| 2007/0156373 A1 | 7/2007 | Yamashita et al. | |
| 2008/0049364 A1 | 2/2008 | Campolo et al. | |
| 2008/0126272 A1 * | 5/2008 | Cunningham | G08B 25/009 706/12 |
| 2008/0209925 A1 | 9/2008 | Pham | |
| 2009/0167494 A1 | 7/2009 | Martins | |
| 2009/0180279 A1 | 7/2009 | Bobbin et al. | |
| 2009/0195349 A1 | 8/2009 | Frader-Thompson et al. | |
| 2010/0026497 A1 | 2/2010 | Choi et al. | |
| 2010/0231407 A1 | 9/2010 | Carr | |
| 2011/0037565 A1 | 2/2011 | Skirble et al. | |
| 2011/0144944 A1 | 6/2011 | Pham | |
| 2012/0001768 A1 | 1/2012 | Radosavljevic et al. | |
| 2012/0126995 A1 | 5/2012 | Sobotka et al. | |
| 2012/0151815 A1 | 6/2012 | Tate | |
| 2012/0223813 A1 | 9/2012 | Baxter et al. | |
| 2012/0246499 A1 | 9/2012 | Jessup et al. | |
| 2012/0319676 A1 | 12/2012 | El-Essawy et al. | |
| 2012/0330473 A1 | 12/2012 | Meredith et al. | |
| 2014/0053260 A1 * | 2/2014 | Gupta | G06F 21/50 726/22 |
| 2014/0165614 A1 | 6/2014 | Manning et al. | |
| 2014/0246924 A1 | 9/2014 | Proud | |
| 2014/0247152 A1 | 9/2014 | Proud | |
| 2014/0324388 A1 | 10/2014 | Kriss | |
| 2015/0169915 A1 * | 6/2015 | Petre | G06K 19/0716 340/10.6 |
| 2015/0346249 A1 | 12/2015 | Sugar | |
| 2016/0012693 A1 | 1/2016 | Sugar | |
| 2016/0379074 A1 * | 12/2016 | Nielsen | H04N 7/181 348/143 |
| 2018/0106532 A1 | 4/2018 | Sugar et al. | |
| 2019/0086449 A1 | 3/2019 | Sugar | |

* cited by examiner

SCATTER PLOT OF ACCUMULATED FEATURE VECTORS

2401

USAGE, CONDITION AND LOCATION TAG AND SYSTEM

CROSS REFERENCE TO RELATED APPLICATIONS

This application claims priority to U.S. Provisional Application No. 62/753,964, filed Nov. 1, 2018, the entirety of which is incorporated herein by reference.

TECHNICAL FIELD

The present disclosure relates to wireless indoor positioning systems that track assets such as medical devices and manufacturing equipment.

BACKGROUND

Real-time location systems (RTLSs) are used to track the location of equipment in healthcare, manufacturing, and other verticals. In an RTLS, small battery-powered tags (referred to herein as active radio-frequency identification (RFID) tags) with built-in wireless transmitters are attached to their associated devices and programmed to periodically emit location beacon signals while wireless sensors at fixed, known positions monitor the incoming transmissions and determine the tag positions in order to locate the associated devices. A well-known downside with current RTLS tags is their inability to provide important contextual information beyond location, such as the usage state (in-use vs. idle) and condition (operating-properly vs. needs-service) of the device. This usage and condition information is useful in many ways, such as: 1) reducing the amount of equipment by eliminating under-used devices, 2) driving efficient device workflows, 3) performing usage-based equipment maintenance, 4) performing condition-based equipment maintenance, and 5) extending equipment lifetimes.

SUMMARY OF THE INVENTION

The present disclosure relates to what is referred to herein as a Usage, Condition and Location System (UCLS) tag, which is an active RFID tag that, in addition to location, is configured to determine the usage state and operating condition of a device. The UCLS tag includes sensors that measure physical activity of the associated equipment (vibration, magnetic activity, temperature, etc.). Algorithms may use the information obtained from the UCLS tags to map the measured sensor data to a contextual usage state and operating condition of the device.

DETAILED DESCRIPTION OF THE INVENTION

Presented herein is a Usage, Condition and Location System (UCLS) and a UCLS tag. The UCLS tag is, in one form, a battery-powered active RFID tag that can be used to determine the physical location, usage state (i.e., whether it is actively being used), and operational condition (i.e., whether it is functioning properly) of a host device to which it is attached. The host device could be a medical device used in a hospital, such as an infusion pump, blood pressure monitor, ventilator, ultrasound imaging machine, hospital bed or wheelchair, or any other device or apparatus whose usage, condition and location is to be monitored. Host devices that have integrated electronics are typically powered from either an AC mains, an internal battery, or both.

Figure 1:
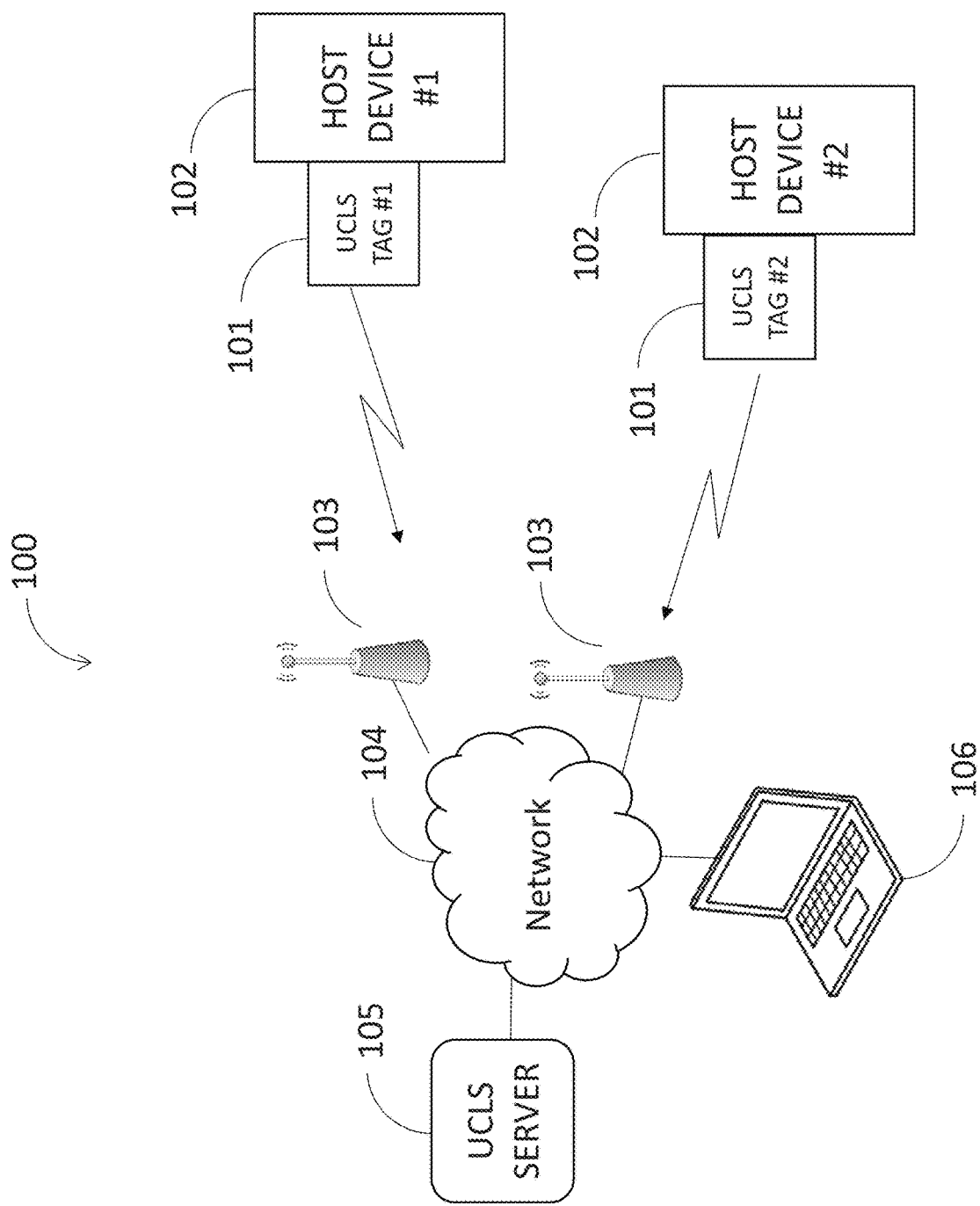
FIG. 1 illustrates a usage, condition and location system (UCLS) that includes one or more UCLS tags, according to an example embodiment.

FIG. 1 illustrates a UCLS 100 that includes multiple UCLS tags 101 attached to host devices 102, with the tags 101 using wireless transmissions to communicate with a UCLS server 105 through one or more wireless network access devices 103 and networks 104. The UCLS tag's wireless transmissions include information such as a media access control (MAC) address to identify the tag, information related to the usage state of the host device, and information related to the operating condition of the host device. The UCLS server 105 is a network server that communicates with and configures the UCLS tags 101, and stores their physical location and transmitted usage and condition information in a database. The UCLS server 105 can later retrieve the stored usage, condition and location information from one or more tags from the database and make it available to one or more UCLS clients 106, which may be personal computers (PCs), tablets, laptops, smartphones, and the like. The network 104 may be a local area network or a wide area network, or a combination thereof.

Figure 2:
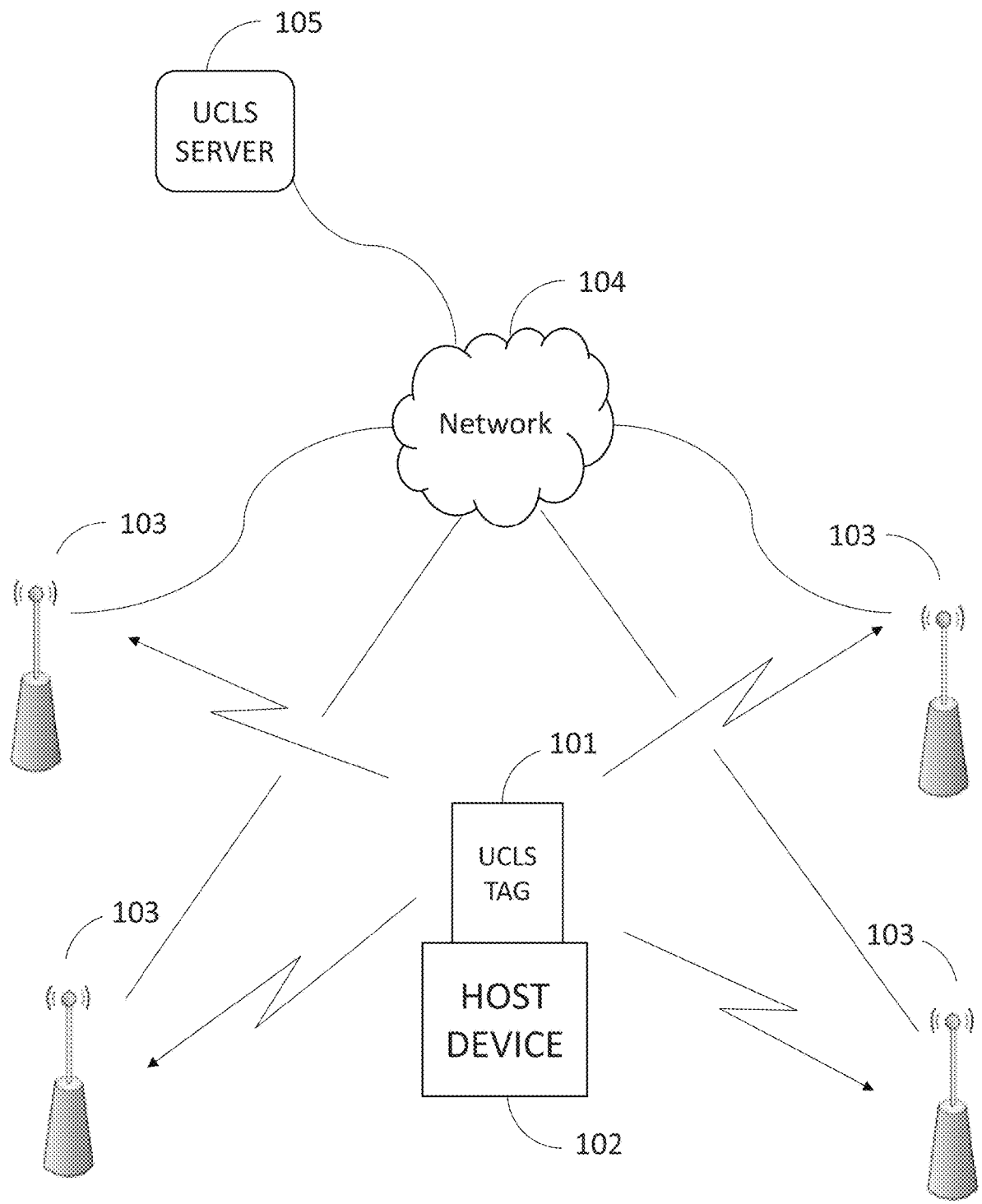
FIG. 2 illustrates a first method for locating a UCLS tag, according to an example embodiment.

Reference is now made to FIG. 2, which depicts a first method for determining the location of a UCLS tag. The UCLS server 105 (shown in FIG. 1) may determine the physical location of a UCLS tag 101 (and therefore the location of its host device 102) by triangulating on the position using received signal strength, angle of arrival or time-of-arrival of its transmissions at one or more network access devices 103.

Figure 3:
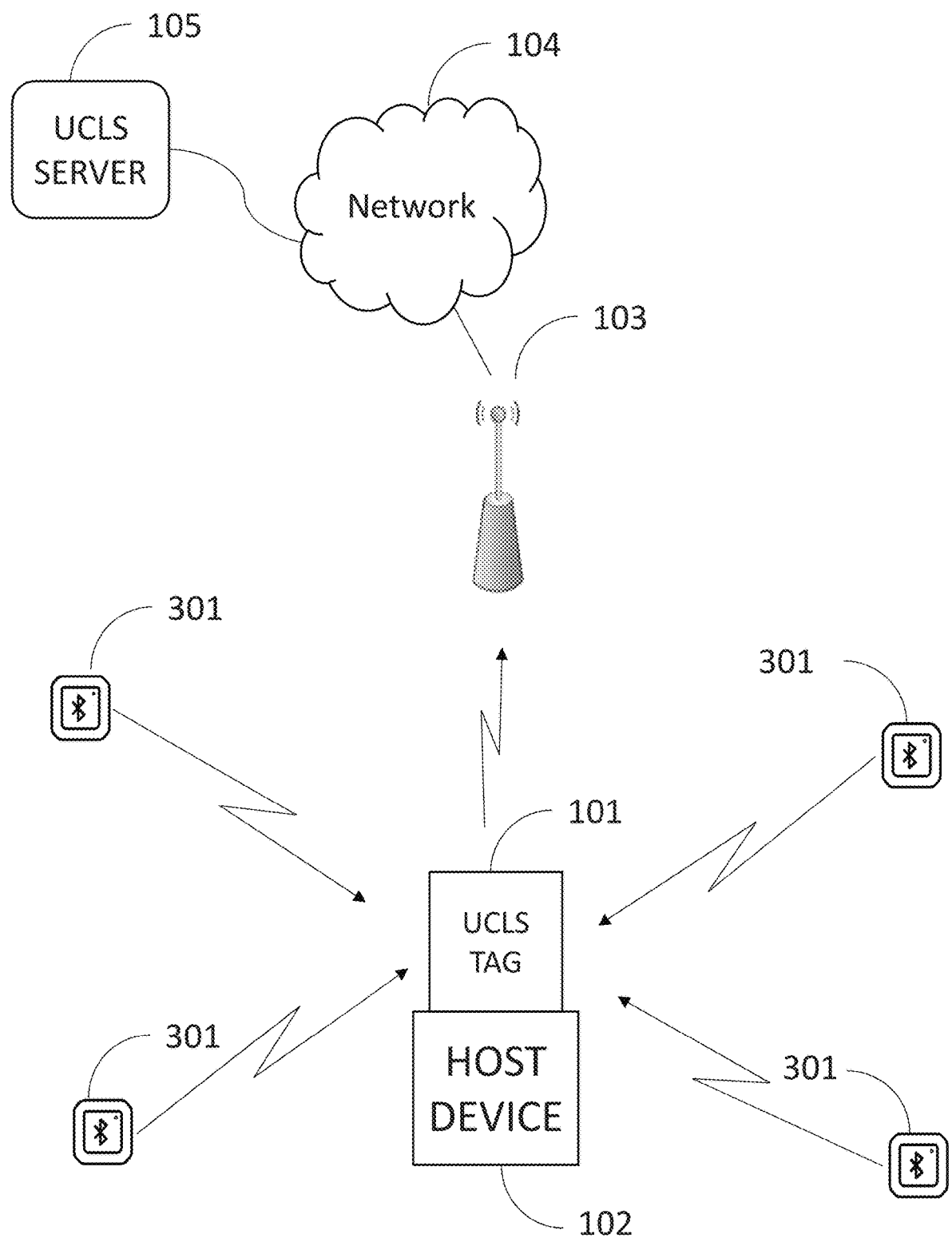
FIG. 3 illustrates a second method for locating a UCLS tag, according to an example embodiment.

Turning now to FIG. 3, a second, alternative method for locating the UCLS tag is to place a number of location transmitters (also known as "location beacons") 301 at various locations within a building/facility where the UCLS tag is deployed. Just before transmitting its MAC address, utilization and condition information to the network access devices 103, the UCLS tag 101 periodically listens for the location transmitters 301, and includes the power-of-arrival, time-of-arrival, or angle-of-arrival of any received packets from the location transmitters 301 in the data packets it sends to the network access devices 103 along with the MAC address, usage information and condition information. The UCLS server 105 could then use the power, time or angle-of-arrival information as well as the known physical location of the location transmitters 301 to determine the location of the tag 101. As a somewhat degenerate example, the UCLS tag 101 may listen for the strongest location transmitter signal and use that transmitter location as the approximate location of the tag.

A sequence number may also be included in the transmissions made the UCLS tag 101. The sequence number could be used at the UCLS server 105 to identify and discard duplicates of the same tag transmission received by multiple network access devices 103. After receiving the host device usage state, condition and location information from the tag's transmissions, the UCLS server 105 could timestamp this data and store it in a database so it can be retrieved and re-used at a later time.

Figure 4:
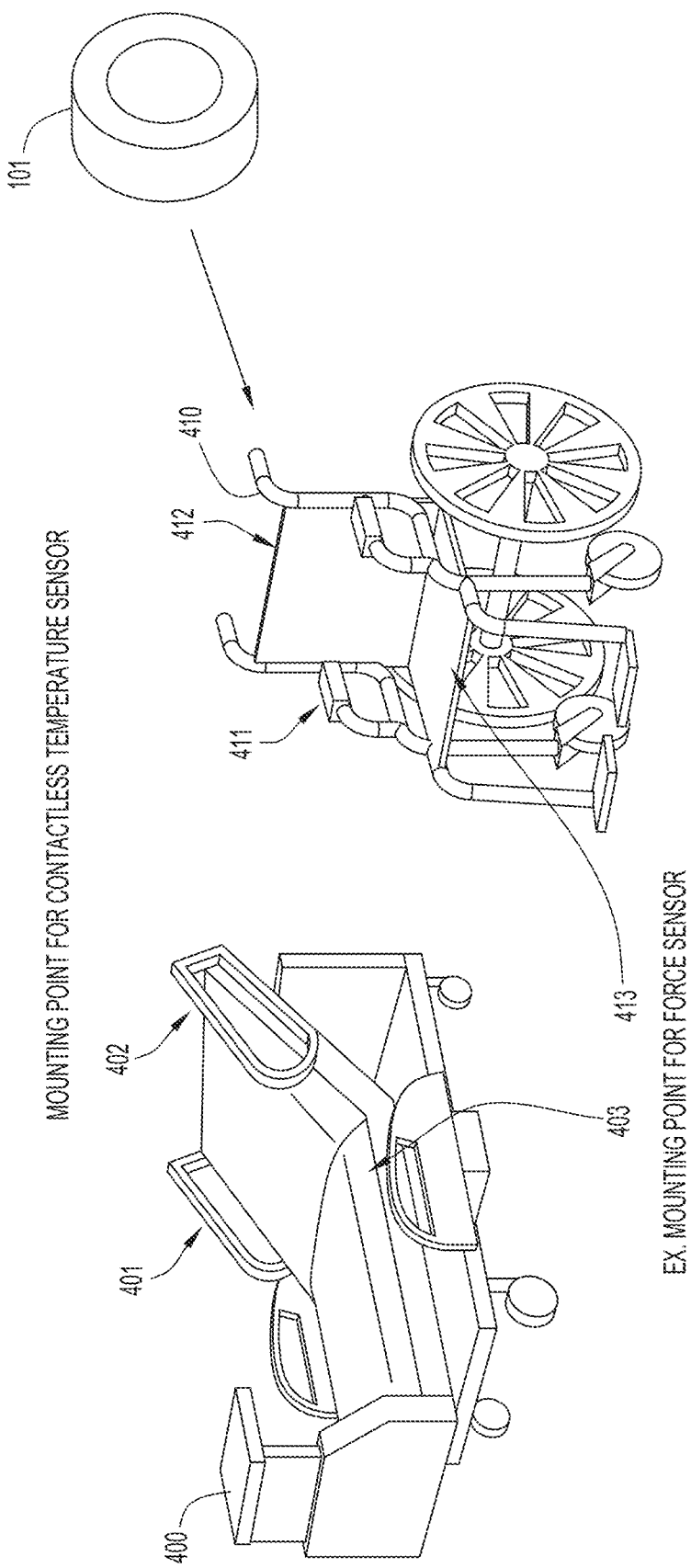
FIG. 4 shows example locations for a UCLS tag or force sensor to be physically mounted on several types of medical devices, according to an example embodiment.

For certain types of host devices, such as hospital beds and wheelchairs, utilization of the device is determined based on the presence of a human occupying the device. The presence of a human can be detected through use of either a contactless temperature sensor (which uses an infrared thermopile to detect a temperature rise when a human is present), a force sensor (which detects a weight change when a human is present), or a proximity sensor (which uses a laser or ultrasound to detect a nearby object or person). The contactless temperature sensor and proximity sensor are available as integrated circuits (ICs) or small circuits that can be soldered onto a printed circuit board inside the tag 101. Force sensors typically reside outside the tag and use a thin connectorized cable to connect to the tag's internal electronics. The tag with integrated contactless temperature sensor or proximity sensor, or the force sensor, may be mounted to the host device. To this end, FIG. 4 shows example locations for the UCLS tag or force sensor to be physically mounted on several types of medical devices. In the case of the hospital bed, the UCLS tag with integrated temperature sensor or proximity sensor may be mounted on the bottom railing 400, the side railing 401, or the top railing 402. The contactless temperature sensor of the UCLS tag is then pointed towards the bed surface to detect a temperature rise when a human is present. Alternatively, in the case of a hospital bed, a UCLS tag with a force sensor may be mounted under the bed mattress 403, and then weight is used to detect presence of the human in the bed. Similarly, for a wheelchair, a UCLS tag with integrated contactless temperature sensor can be mounted on the back railing 410, the arm 411, or the top of the back cushion 412, with the temperature sensor pointed towards the seat surface to detect a temperature rise when a human is present. Alternatively, for the wheelchair, a UCLS tag with a force sensor may be mounted under the seat surface 413, and then weight is used to detect the presence of the human in the wheelchair.

Figure 5:
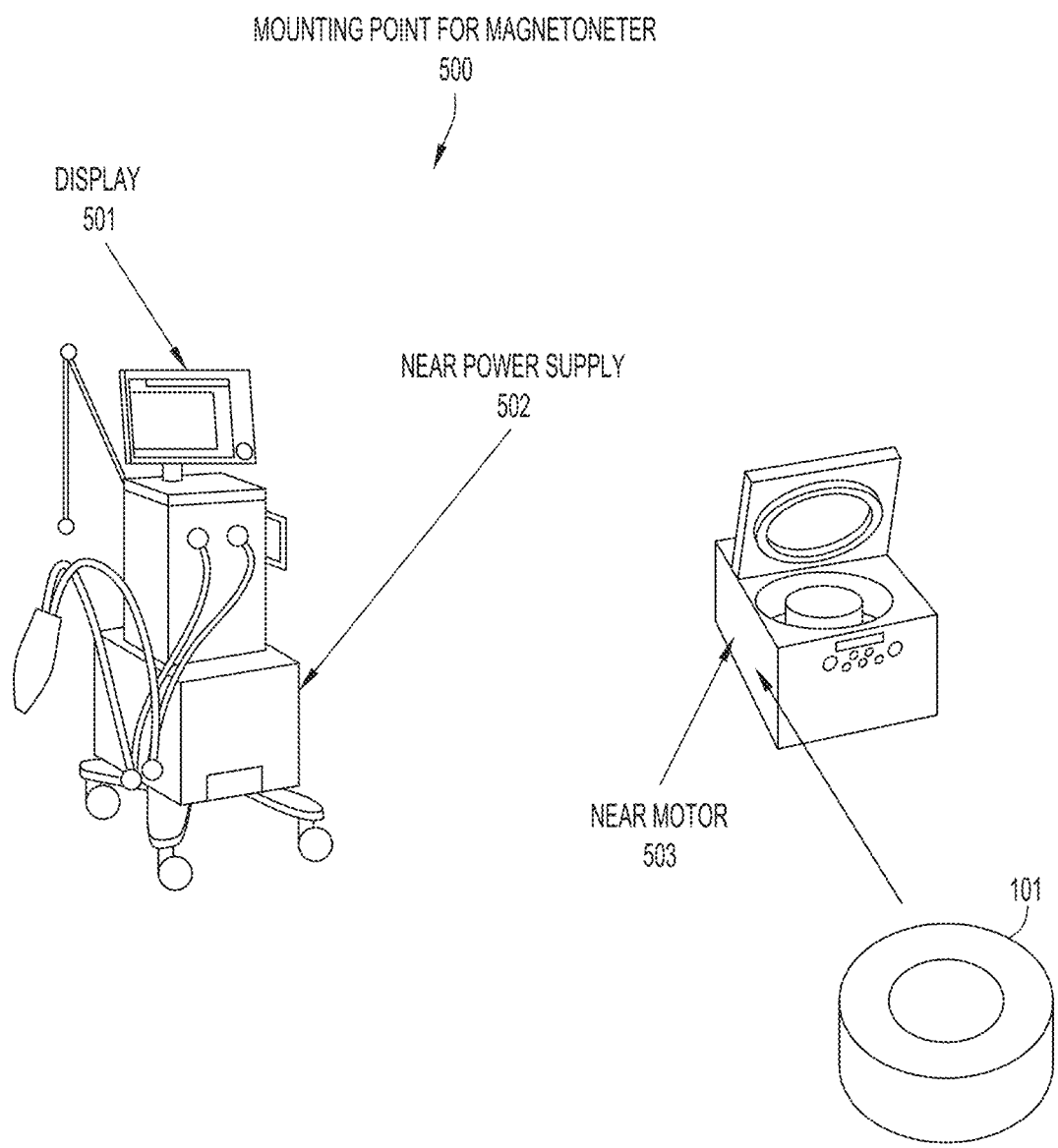
FIG. 5 shows example locations where a UCLS tag can be mounted to a device to best capture magnetic activity associated with the device, according to an example embodiment.

For medical devices that have a motor or electronic circuit board, such as ventilators and centrifuges, utilization of the device may be determined by the pattern of magnetic energy emitted by the device from operation of an electric motor or electronic circuit board. The magnetic energy can be detected through use of a magnetometer embedded in the UCLS tag 101. FIG. 5 shows example locations of a mounting point 500 where the UCLS tag 101 (including magnetometer) can be mounted to a device to best capture magnetic activity that allow detection of device utilization. In the example of the ventilator, the UCLS tag can be mounted near the device display 501 (which includes an electronic circuit board) or as shown at 502, near the device power supply (which also includes an electronic circuit board with an on-board AC-to-DC converter). In the example of the centrifuge, the UCLS tag can be mounted near the electric motor 503.

Figures 6A, 6B:
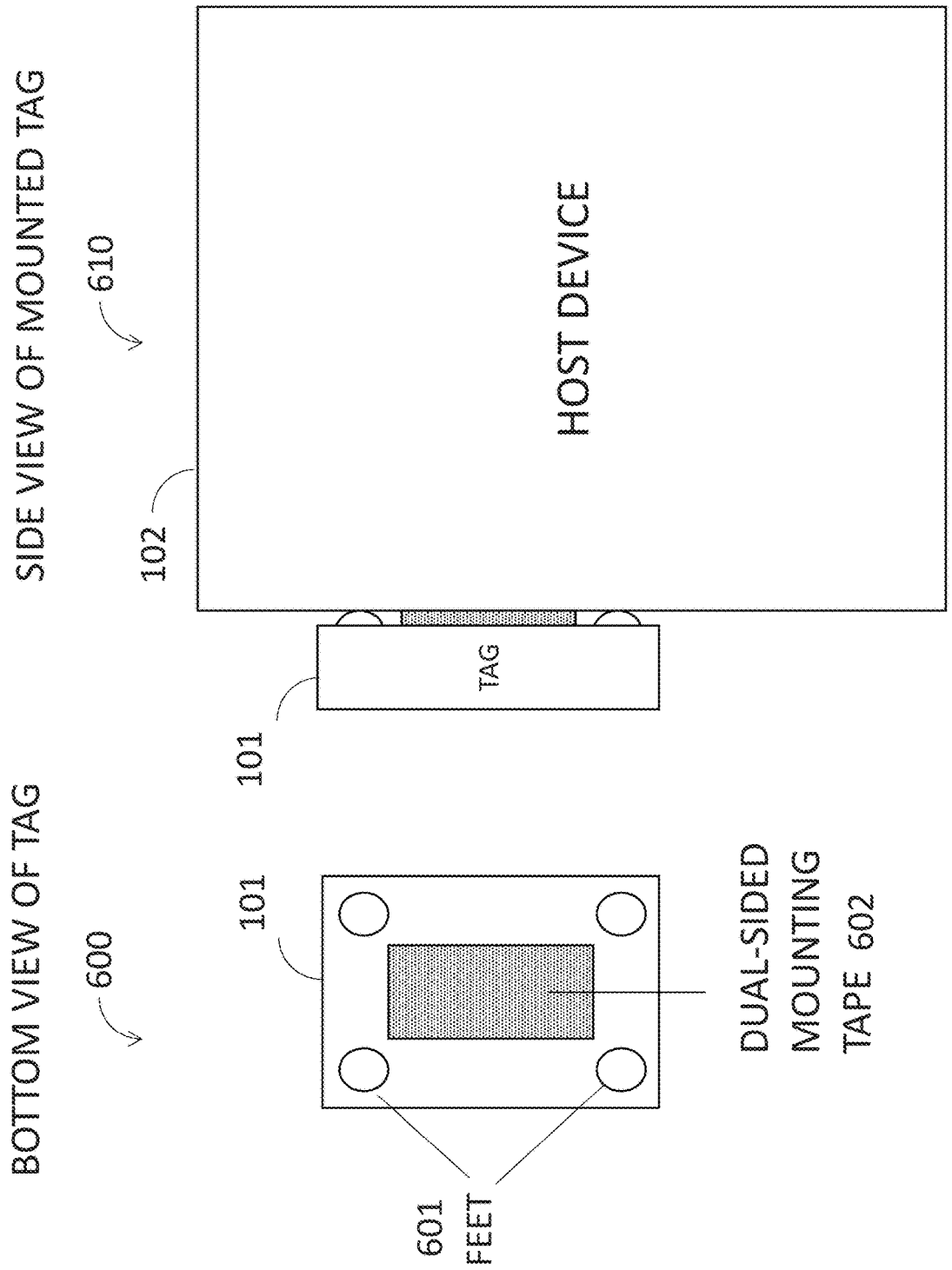
FIGS. 6a and 6b show a technique for adding rigid feet on the bottom of the UCLS tag to prevent double-sided mounting tape (or other pliant affixing material) from damping host device vibrations from being detected by an accelerometer on the tag, according to an example embodiment.

Reference is now made to FIGS. 6 and 6*b*. FIG. 6*a* shows a bottom view 600 of the UCLS tag 101, and FIG. 6*b* shows a side view 610 of a mounted UCLS tag 101. Many motorized devices are known to exhibit vibrational behavior caused by the rotations of their motors. These vibrations can be detected by accelerometer sensors included in the UCLS tag. In these scenarios, the UCLS tag 101 is mounted to the enclosure of host device 102. In one instantiation, dual-sided mounting tape is used to affix the tag to the device enclosure. In embodiments where the UCLS tag 101 uses an integrated accelerometer to detect usage or condition activity by measuring vibrations of the host device, to prevent the dual-sided tape 602 (or other pliant affixing material) from dampening the vibrations seen by the tag's accelerometer, the UCLS tag 101 includes rigid feet 601 that make direct contact with the enclosure. The vibrations of the host device are therefore transferred directly through these rigid feet to the body of the UCLS tag, and correspondingly to the tag's accelerometer, which is typically a small integrated circuit soldered to an internal printed circuit board of the UCLS tag.

Figure 7:
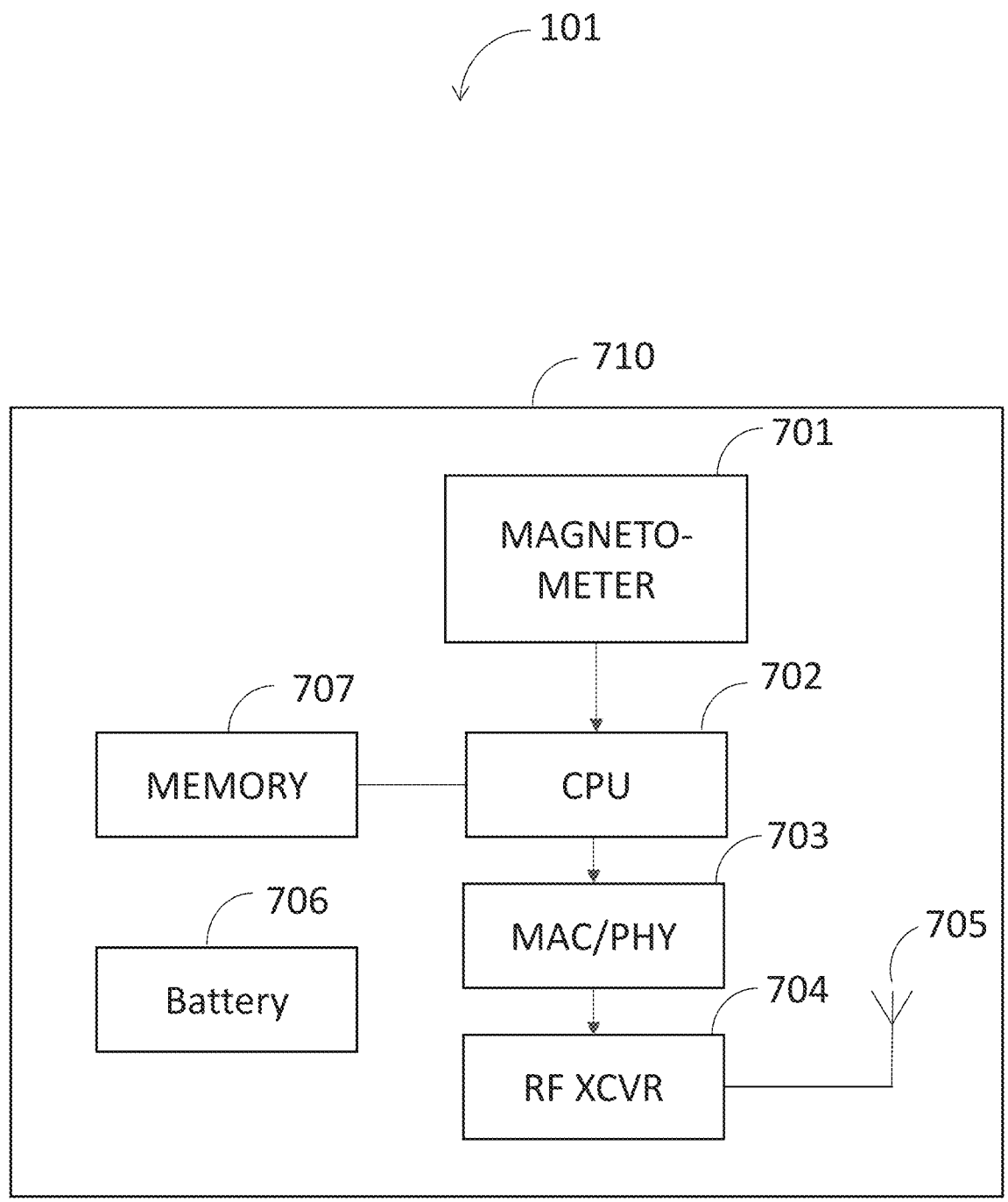
FIG. 7 shows a block diagram of a UCLS tag, according to an example embodiment.

Turning now to FIG. 7, a block diagram of the UCLS tag 101 is shown. The UCLS tag could include electronics such as a battery 706, a central processing unit (CPU) 702, a memory 707 containing computer instructions and data, a magnetometer 701, and a wireless transceiver comprising a MAC/PHY module 703, an RF transceiver 704 and an antenna 705 to exchange data with communications network 104 via wireless network access devices 103 (as shown in FIG. 1). The magnetometer (magnetic field sensor) 701 could be a single or multi-axis hall-effect sensor IC, a single or multi-axis e-compass such as those used in a smartphone, or similar. The magnetometer 701 may have a noise level of approximately 1 microtesla root mean squared (RMS) and able to sample the magnetic field strength with uniformly spaced samples at a sampling rate of 100 Hz or higher on each of its supported axes. The electronics of the UCLS tag 101 may be stored inside a metal or plastic enclosure 710. The wireless (RF) transceiver 704 may be configured to use a protocol such as Bluetooth 5™ to communicate with network access devices 103.

For some electronic host devices, a higher frequency magnetometer may be more appropriate. Hall-effect sensor integrated circuits (ICs) with bandwidths of up to 10 MHz are commercially available. Such hall-effect ICs typically have analog outputs that can be digitized using a high-speed ADC with a sampling rate of up to 20 MHz. Even higher frequency magnetometers could be constructed using a simple wire loop inductive antenna element feeding (optionally) an amplifier followed by a high-speed ADC. Even higher magnetic frequencies can be observed by placing a tunable RF downconverter between the inductive antenna and the ADC.

The UCLS tag 101 may use magnetometer 701 to determine when an electrically powered host device is actively being used. For example, infusion pumps typically use an electric motor to deliver fluid to a patient—by either depressing a syringe, driving a piston, or squeezing an elongated tube using rollers. When the pump is turned on, the change in magnetic field caused by energizing the electric motor can be detected by the magnetometer 701. Another example device is a battery or AC-powered blood pressure monitor, which typically uses a DC motor to drive a piston to push pressurized air into a blood pressure cuff.

Figure 8:
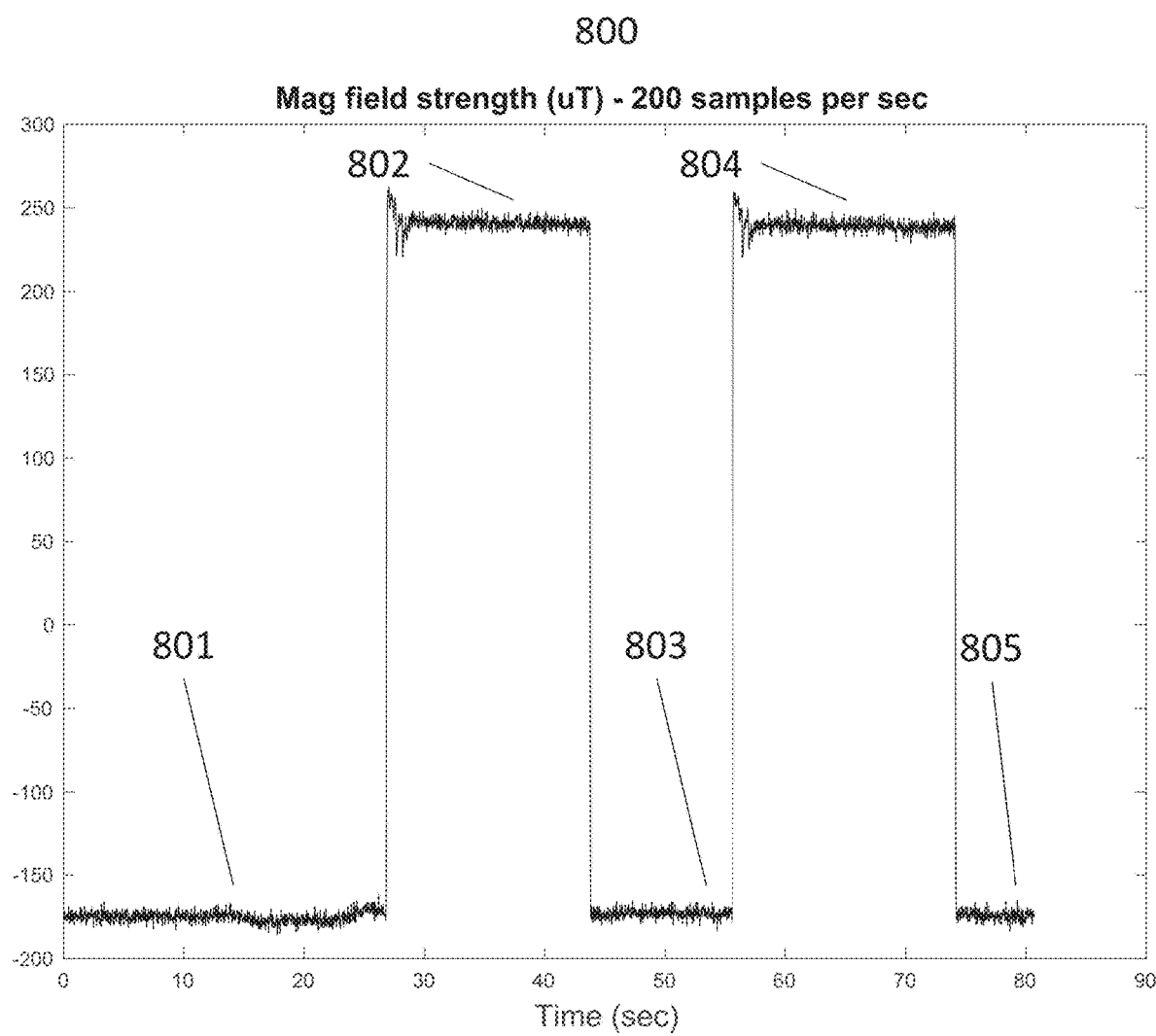
FIG. 8 shows magnetometer samples taken at 200 samples-per-second from a UCLS tag attached to a battery-powered blood pressure monitor over a period of time, according to an example embodiment.

FIG. 8 shows a plot 800 of magnetometer samples taken at 200 samples-per-second from a UCLS tag attached to a battery-powered blood pressure monitor over a period of approximately 80 seconds. Segments 801, 803 and 805 show the magnetic field when the blood pressure monitor is powered on, but not actively being used. Segments 802 and 804 show the magnetic field during a measurement, while the blood pressure cuff is being pressurized via the DC motor. The plot 800 shows that there is clearly a significant change in DC level of the magnetic field while the blood pressure monitor is actively being used vs. otherwise. This is to be expected because of the way DC motors are known to behave—i.e., they use DC current to drive an electromagnet, which in turn causes a magnetic rotor to spin and move a piston. The change in DC level seen in segments 802 and 804 indicates when the electromagnet is being energized.

In addition to infusion pumps and blood pressure monitors, magnetometer 701 may be employed to detect usage activity in other types of electronic equipment that use an electric motor, such as ventilators, continuous positive airway pressure (CPAP) and bi-level positive airway pressure (BiPAP) breathing devices, centrifuges, hospital beds with electronically pressurized air compartments, and the like. Also, since temporal changes in electrical current are known to produce time-varying magnetic fields, magnetometer 701 could be used to detect time-varying electrical activity (and therefore usage activity) in virtually any electronic device—even those that are not necessarily motorized—such as LED screens, ultrasound machines, defibrillators, and X-ray machines.

Figure 9:
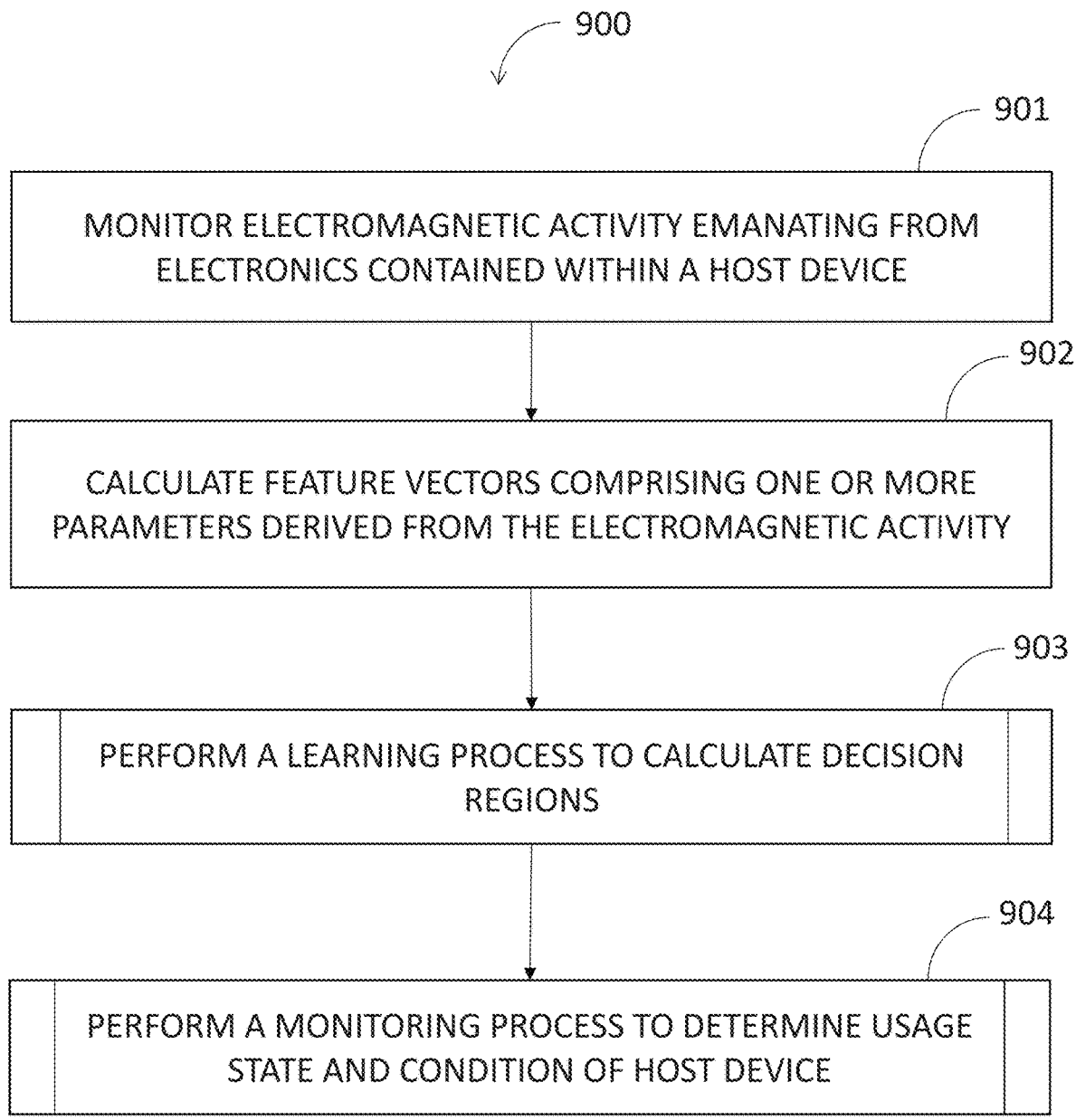
FIG. 9 illustrates a flow chart of a method for learning a host device's operating characteristics and monitoring the host device for usage or condition changes, according to an example embodiment.

Reference is now made to FIG. 9, which shows a flow chart of a method 900 for learning a host device's operating characteristics and monitoring for usage or condition state changes. At 901, a device such as a UCLS tag 101 uses a magnetometer to monitor electromagnetic activity coming from electronics contained within a host device. At 902, feature vectors based on the monitored electromagnetic activity are calculated. The feature vectors contain electromagnetic properties of the host device based on the magnetometer measurements. The feature vector could include parameters for any of the following: mean, maximum, minimum, median or RMS of the magnetic field strength computed over a period of time; fundamental frequency, harmonic weighting, spectral envelope, period, duty cycle, peak□to-average power ratio of the magnetic field strength measurements computed over a period of time; or measured power at a detected fundamental frequency and harmonics thereof of the magnetic field measurements. The feature vectors can be computed either directly on the tag 101 or on a computer outside the tag. For example, the feature vectors might be computed on a server, e.g., UCLS server 105, in the cloud using magnetometer data sent wirelessly from the UCLS tag 101. At 903, a learning process is used to calculate decision regions that can be used to determine when the host device is actively being used. At 904, a monitoring process is used to determine the usage state and condition of the host device using the feature vectors and learned decision regions.

Figure 10:
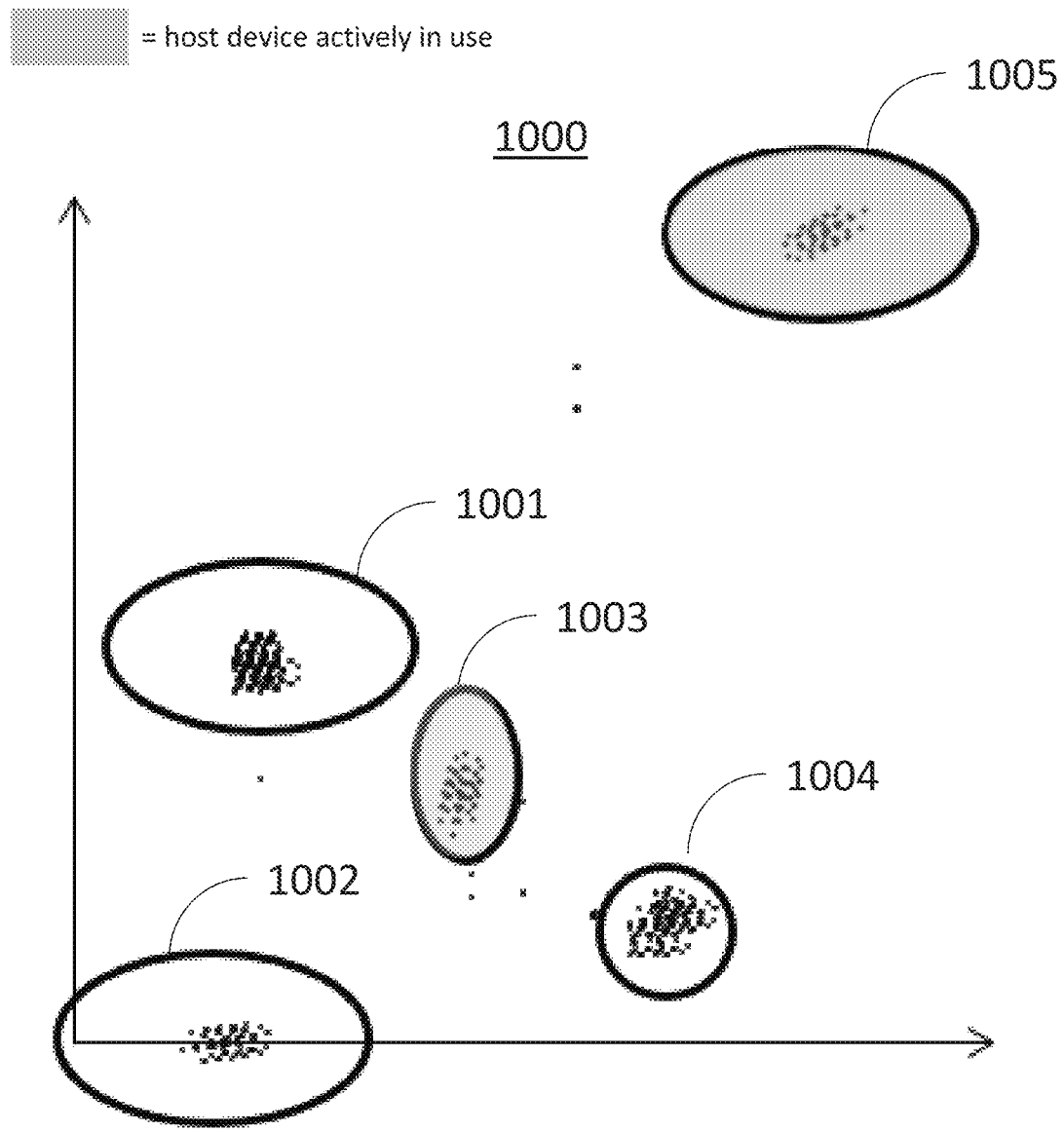
FIG. 10 shows an example scatter plot of accumulated feature vectors taken from a fictitious host device, according to an example embodiment.

Turning now to FIG. 10, an example scatter plot 1000 of accumulated feature vectors taken from a fictitious host device is shown. In this example, each feature vector has 2 components represented on the X and Y axes. The two components are, for example, RMS magnetic field strength and magnetic field fundamental frequency, or RMS magnetic field strength using two different averaging durations. It should be noted that the use of exactly 2 dimensions in this example is only to make the concepts described herein easier to visualize. For some host devices, it may be sufficient to use only a single dimensional feature vector (e.g., RMS magnetic field strength only). In other cases, the feature vector dimensionality could be much larger than 2, especially when the UCLS tag 101 is equipped with other sensors in addition to the magnetometer 701.

The scatter plot shows feature vectors taken from a UCLS tag attached to the host device over a long period of time—long enough for the host device to have been configured to run in each of its operate operating states (or at least each of its most frequently used operating states) for a significant period of time, allowing clusters of proximately located feature vectors to appear in the plot. In FIG. 10, the clusters appear in regions 1001 through 1005. If the UCLS tag 101 is properly positioned on the host device to pick up magnetic activity, and the feature vector components and their associated parameters are selected properly for the host device, the clustering will often be indicative of the operating state of the host device. The clustering occurs because host devices typically configure their electronics to use a specific set of parameters while in any fixed operating state, so that they give off a fairly constant electromagnetic fingerprint while in that state, thereby causing feature vectors obtained from the magnetometer samples to accumulate and cluster in one region in the plot 1000. If the host device is a blood pressure monitor, for example, feature vectors might gather in region 1001 when the monitor is charging its battery but not actively being used. Clustering in region 1002 might occur when the monitor is powered off. Clustering in region 1003 might occur when the monitor is completing a test and releasing pressurized air from its cuff. Clustering in region 1004 might occur when the monitor is generating audio sound through its speaker to indicate an error condition. Clustering in region 1005 might occur when the monitor is actively pumping pressurized air into the cuff. Some of these clusters, in regions 1003 and 1005 in particular, which are shaded in FIG. 10, contain feature vectors that are associated with the blood pressure monitor in an "actively being used" state. The remaining clusters are associated with the monitor in a "not actively being used" state.

The term "operating space" for a particular host device with a UCLS tag attached, is used herein to refer to the set of all points in Euclidean N-space (where N is the number of feature vector components) in which a host device is known to produce feature vectors, assuming it is in a good operating condition. The operating space can be found by attaching a UCLS tag to a host device, configuring the tag to continuously generate and store feature vectors, and allowing the host device to operate for a very long time in any and all of its known operating states. The scatter plot of FIG. 10 shows an operating space for a fictitious host device for N=2. The term "in-use operating space" refers to a subset of the operating space containing all feature vectors that the host device is known to produce while in an in-use operating state. The remaining feature vectors in the operating space comprise the "not in-use operating space".

Figure 11:
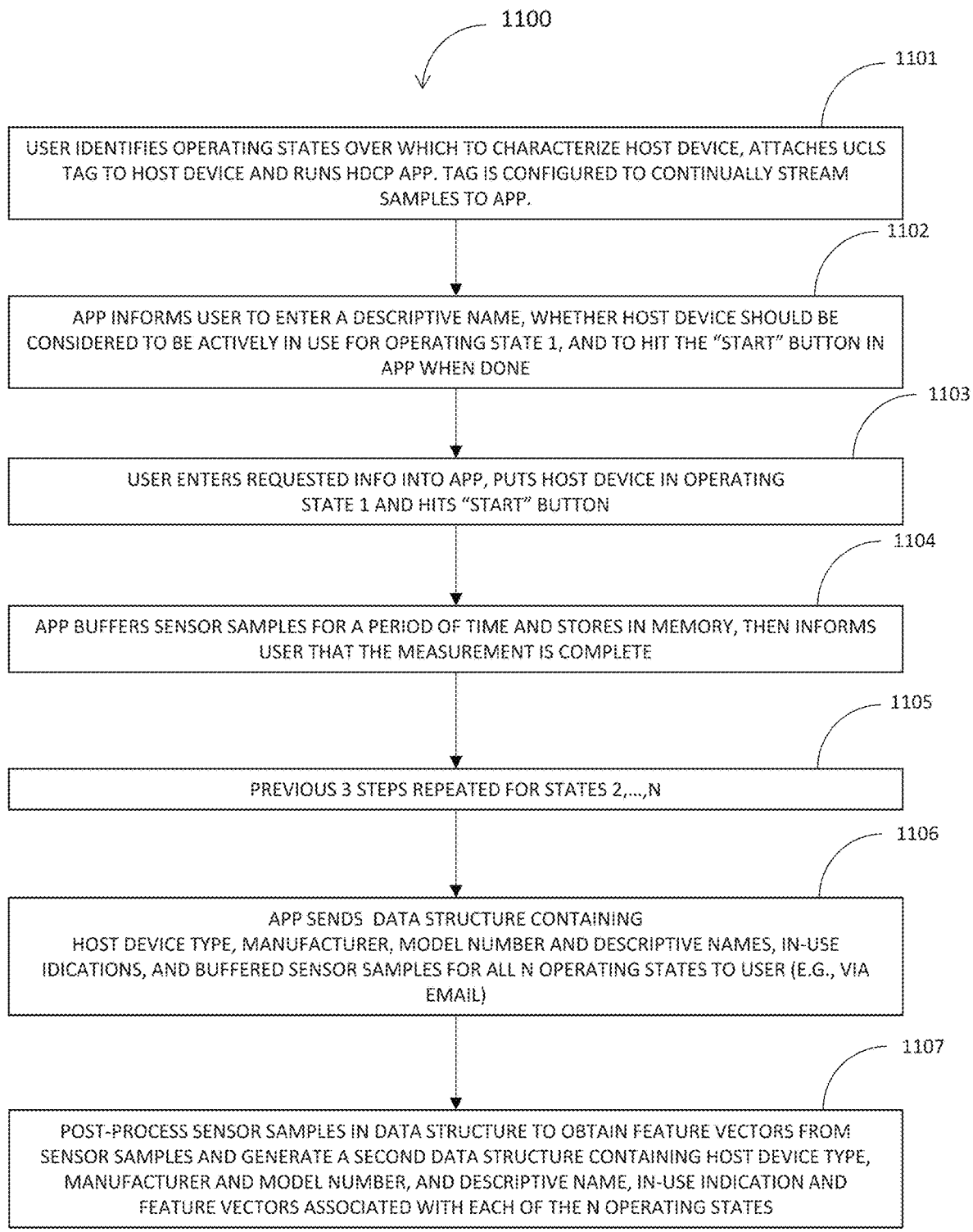
FIG. 11 shows a flow chart for a host device characterization procedure, according to an example embodiment.

Reference is now made to FIG. 11, where a host device characterization procedure (HDCP) 1100 is described. The HDCP 1100 is a method for obtaining an estimate of the operating space and in-use operating space for a host device with a UCLS tag attached. The procedure 1100 is driven by a PC, smartphone, or tablet software application that communicates with the tag using a protocol like Bluetooth 5™, and with a human user to provide ground truth information about the known operating state of the host device. At 1101, the user first identifies all host device operating states that should be included in the characterization procedure, and if necessary, learns or reviews how to put the host device into each of these states. The user then attaches a UCLS tag 101 to the host device 102 and runs the HDCP software application (the "App"). The tag could be configured into a special HDCP mode in which it continuously streams samples from its magnetometer 701 to the App. At 1102, the App prompts/asks the user to put the host device into its first operating state, to enter a descriptive name for this state (e.g., "powered off", or "powered on, idle"), whether the host device should be considered to be actively in use while in this state, and to hit the "Start" button to begin storing magnetometer samples on the App. At 1103, the user enters the requested data and hits the "Start" button in the App. At 1104, the App accumulates magnetometer samples in memory over a period of time, and then notifies the user once a sufficient number of samples have accumulated. At 1105, operations 1102-1104 are repeated for each of the remaining host device operating states. At 1106, when the measurements have been completed for each operating state, the App sends the user a data structure containing the host device type, manufacturer and model number, as well as the descriptive name, in-use indication and magnetometer samples for each operating state to the user—e.g., via email. At 1107, the data structure is post-processed (e.g., using a software tool like Matlab™) to generate feature vectors from the sensor samples. Post-processing also includes accumulating and storing the feature vectors obtained from the sensor samples for each of the host device operating states used in the procedure. The feature vectors obtained while the host device was in-use are labeled as such. When the feature vectors have been generated, a second data structure can be generated containing the host device type, manufacturer and model number, and for each operating state: the descriptive name, in-use indication and feature vectors. This second data structure contains the operating space and in-use operating space estimates.

The operating space and in-use operating space estimates generated by procedure 1100 can be used to determine whether the UCLS tag 101 is properly positioned on the host device to pick up magnetic activity, whether the feature vector components and their associated parameters are selected properly for the host device, and whether other sensors in addition to the magnetometer are needed in the feature vector space to reliably determine the host device usage state. Indeed, in order for method 900 to perform properly, it is critical that any feature vectors obtained while the host device is in an in-use operating state do not overlap with feature vectors obtained from a not-in-use operating state, since if this happened, the system may not be able to determine whether the host device was in use or not based on observations of the feature vector values alone. For example, referring back to FIG. 10, if the feature vectors in region 1001 (a not-in-use state) overlapped with those from region 1003 (an in-use state), then it would be impossible to reliably determine usage state from the feature vectors. If there are cases when there is overlap between in-use and not-in-use clusters, then the feature vectors may be redefined—either by changing the feature vector components or parameters, or by using information from other sensors in the feature vector definition—in order to eliminate the overlap. The latter is described hereinafter in more detail.

Figure 12:
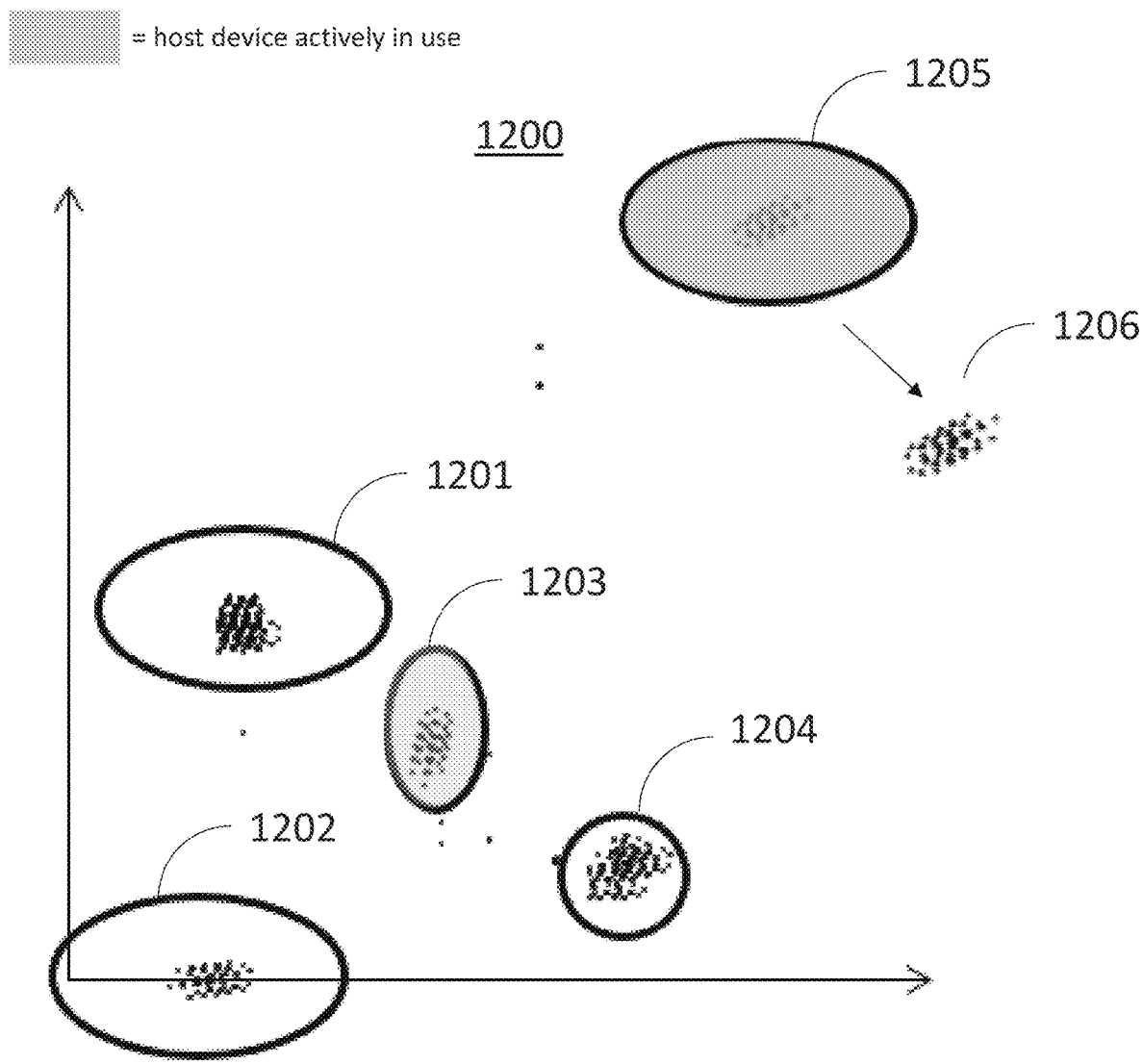
FIG. 12 shows how the example scatter plot of FIG. 10 might appear after a host device malfunction, according to an example embodiment.

Reference is now made to FIG. 12, which shows a scatter plot 1200 having clusters 1201, 1202, 1203, 1204 and 1205 similar to the scatter plot of FIG. 10, with an additional cluster 1206 added to illustrate how a change in the operating condition (e.g., due to a malfunction or degradation in performance) of the host device might appear in the diagram. When the host device is operating normally, its scatter diagram will appear as shown in FIG. 10, or equivalently, in FIG. 12, with the points in cluster 1206 removed. After a malfunction, one or more of the clusters may change position. In this example, the feature vectors that previously accumulated in cluster 1205 may begin to accumulate in cluster 1206 instead. While a significant malfunction could cause a sudden shift in the cluster position, a gradual degradation in the host device's condition might cause the cluster centroid to drift more gradually. For some malfunctions there may even be a change in the number of clusters. There could also be a change in the size or shape of one or more clusters in addition to a change in centroid position. In any of these scenarios, the change in the cluster statistics can be detected, and reported as anomalous to an interested observer. If the alert turns out to be a false alarm, the feature vectors causing the alert could be fed back as non-anomalous data into the learning process 903 to prevent them from causing similar alerts in the future.

Figure 13:
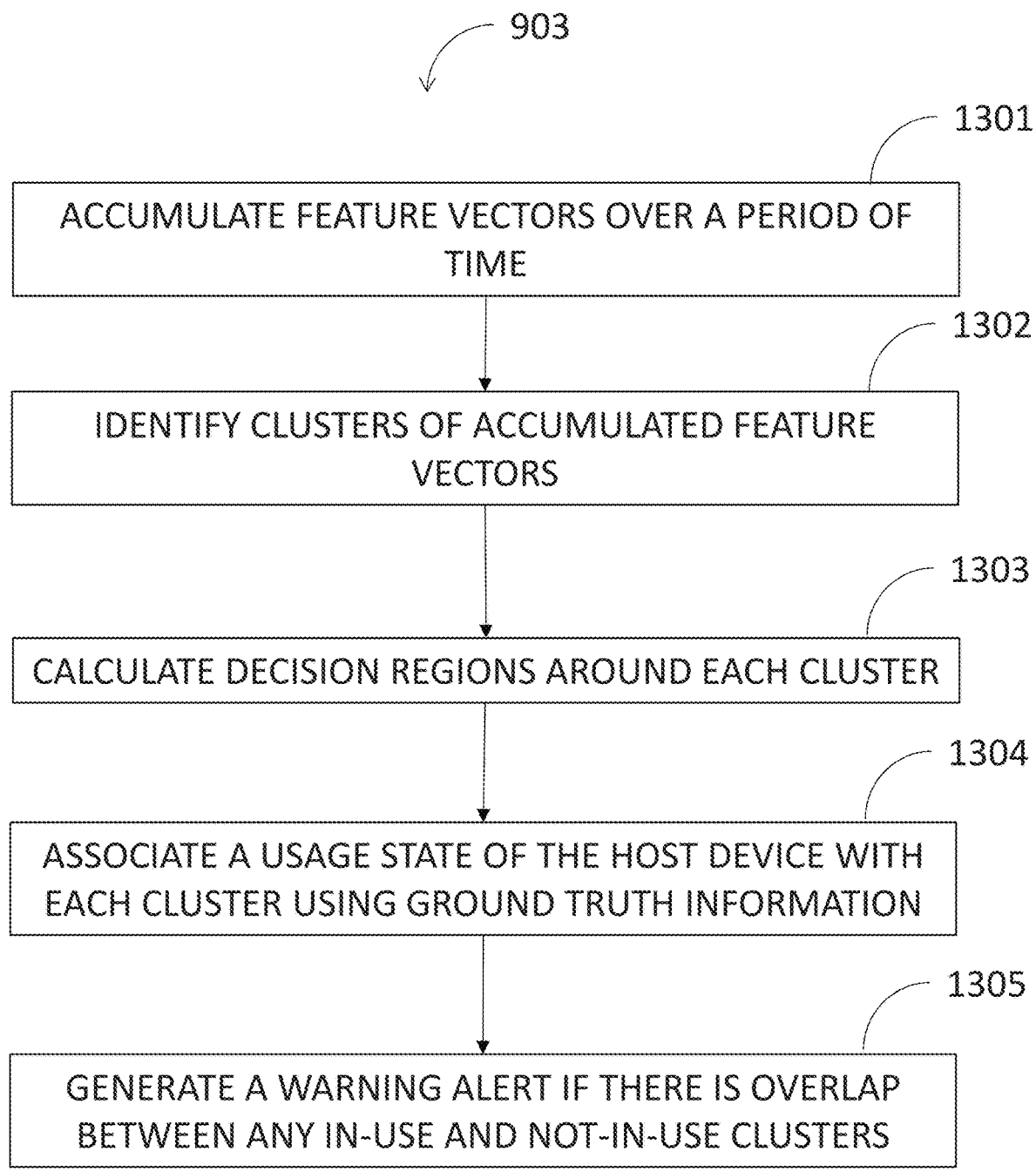
FIG. 13 illustrates a flow chart of a learning process for learning to identify a host device's usage and condition state based on observations of feature vectors derived from tag sensor data, according to an example embodiment.

Reference is now made to FIG. 13, where the learning process 903 is described. At 1301, feature vectors computed in 902 (of FIG. 9) are accumulated over time. At 1302, clusters of accumulated feature vectors are identified. Any one of a well-known number of clustering algorithms described in computer science textbooks could be used to identify the clusters, such as K-Means, Density-based Spatial Clustering of Applications with Noise (DBSCAN), Mean-Shift Clustering, or Agglomerative Hierarchical Clustering. These algorithms typically support an arbitrary number of feature vector dimensions, so there is no reason to limit the dimensionality for any reason—even if multiple sensors are used in addition to the magnetometer. At 1303, a decision region is calculated for each cluster identified in step 1302. The decision regions could be used as part of the monitoring process 904 (FIG. 9) to determine whether a feature vector occupies a particular cluster. At 1304, a usage state of the host device is associated with each cluster using ground truth information. The ground truth information could be obtained using a procedure like the HDCP procedure 1100. At 1305, a determination is made as to whether there is any significant overlap between any in-use and not-in-use regions, and if there is any detected overlap, generating a warning indication to bring attention to the overlap. If a feature vector dimensionality of 3 or less is used, the overlap detection could be done by visual inspection of a scatter plot obtained through the host device characterization procedure 1100, using color coding to differentiate in-use vs. not-in-use feature vectors, and looking for any clusters containing points with both colors. If more than 3 dimensions are used, the overlap detection could be done using a straightforward multi-dimensional search for overlap among the feature vectors, the clusters or their boundary information obtained from the clustering procedure at 1302.

Once the learning process has been completed for a particular host device, the host device type, manufacturer, model number, any installation notes for the tag (including where to position the tag on the host device), the feature vector definition (i.e., concise definition for each feature vector component and how it is to be computed), the number of clusters in its operating space, and the decision regions and in-use indication for each cluster can be stored in a database on the UCLS server 105. When a new UCLS tag is associated with the same or similar host device in the future, instead of repeating learning process 903, the installation notes, feature vector definition, number of clusters, decision regions and in-use indication for each cluster could be retrieved from the database and programmed into the tag.

Figure 14:
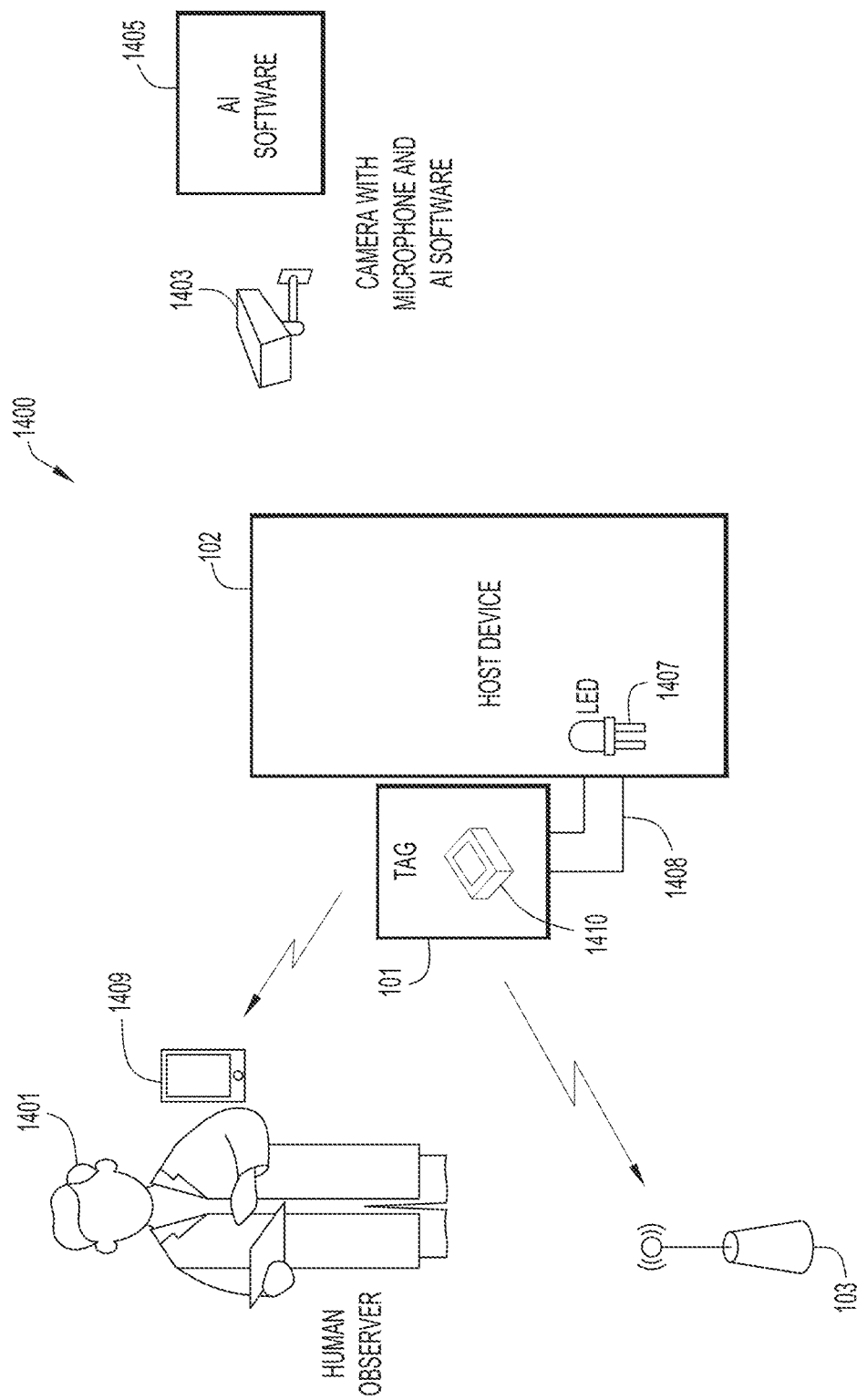
FIG. 14 illustrates several methods for obtaining ground truth information that can be used in the learning process, according to an example embodiment.

Reference is now made to FIG. 14, which illustrates a number of methods 1400 for obtaining ground truth information that could be used at 1304 of learning process 903, of FIG. 13. The ground truth information could come from a human observer 1401 with a smartphone or tablet computer 1409 who attaches a UCLS tag 101 to the host device 102 and configures the tag to stream sensor measurements to the smartphone. The human observer 1401 could enter operating state and usage state information into the smartphone while the smartphone buffers and stores the sensor samples. This is the HDCP procedure 1100 described earlier. Alternatively, if the UCLS tag 101 is equipped with a red green blue (RGB) color sensor 1410 with a lens on its enclosure, a light pipe 1408 could be used to carry light from an LED 1407 on the host device to the RGB color sensor 1410 embedded in the tag 101. If the LED 1407 is known to indicate the usage state of the host device, then monitoring the LED using the RGB color sensor 1410 through the light pipe 1408 would allow the UCLS tag 101 to determine whether the host device is actively being used during the learning process 903 without requiring human interaction. Another approach would be to observe the host device using a camera 1403 while it is being used. The recorded video and/or audio from the camera 1403 may be analyzed by a human to provide the ground truth information. This technique could be automated using artificial intelligence (AI) software 1405 to assess the host device usage state from the audio and video instead of a human. Yet another technique would be to have the UCLS tag 101 use its microphone to store and forward digitized audio segments before and after any feature vector changes are detected from the host device. The audio segments could be forwarded to a server along with the feature vectors and/or raw sensor samples and used to determine ground truth by listening for verbal hints as to what the host operator was doing with the host device before and after the operating state transition.

Figure 15:
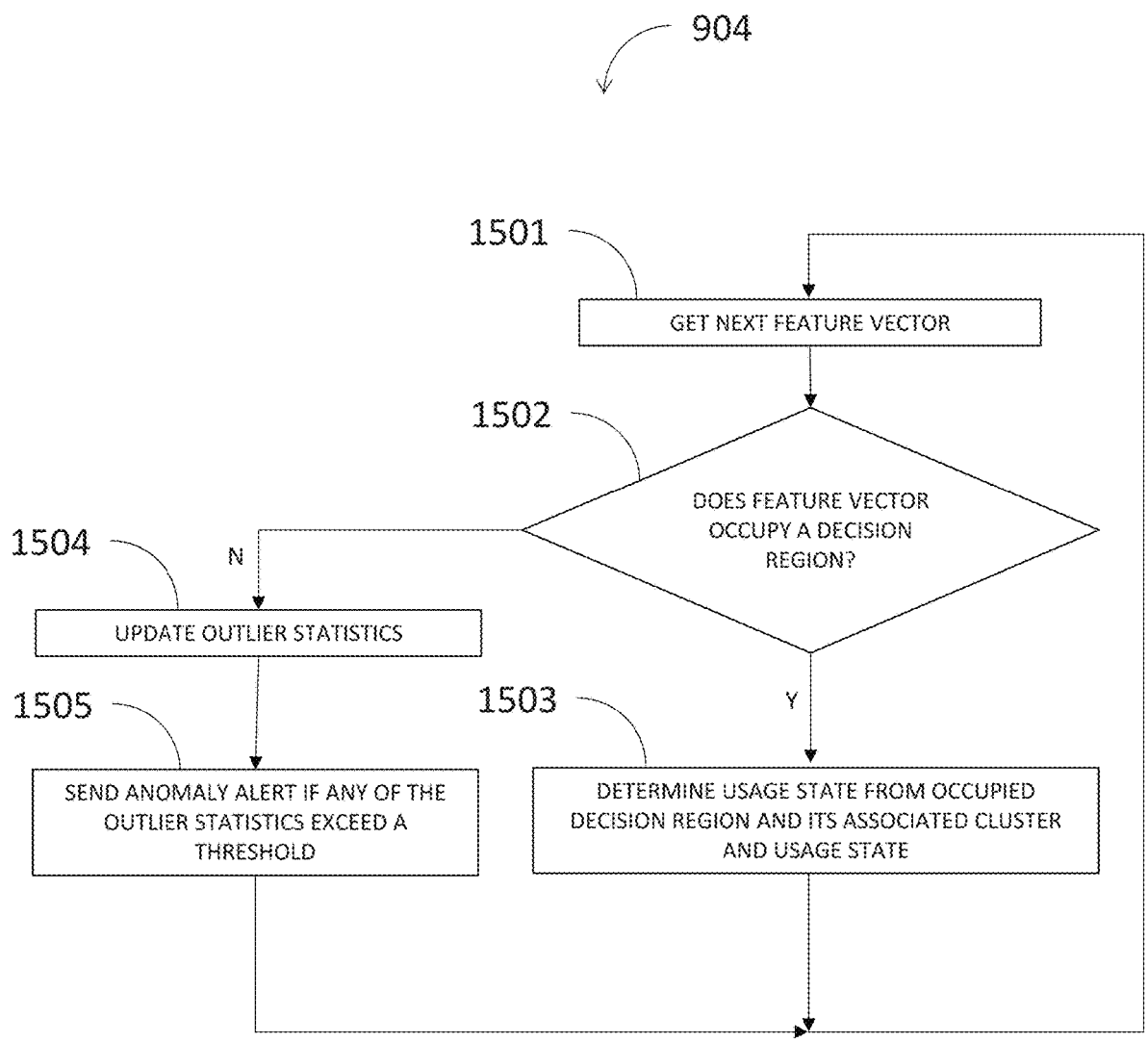
FIG. 15 illustrates a flow chart of a monitoring process for determining a host device's usage and condition state based on observations of feature vectors derived from tag sensor data, and decision regions calculated in the learning process, according to an example embodiment.

Turning now to FIG. 15, a flow chart depicting the monitoring process 904 is shown. At 1501, a new feature vector is obtained based on the most recently received set of magnetometer samples. At 1502, a determination is made as to whether the feature vector occupies any of the decision regions computed at 1303 of the learning process (FIG. 13). If the feature vector occupies a decision region, at 1503 the usage state for the host device is assigned based on the usage state associated with the occupied decision region. If the feature vector does not occupy any of the decision regions, control transfers to 1504, where outlier statistics get updated when an outlier is found. At 1505, if any of the outlier statistics exceeds a threshold, an anomaly indication is sent indicating a possible malfunction of the host device. The next step in the monitoring process is to return to 1501 to get another new feature vector.

Figure 16:
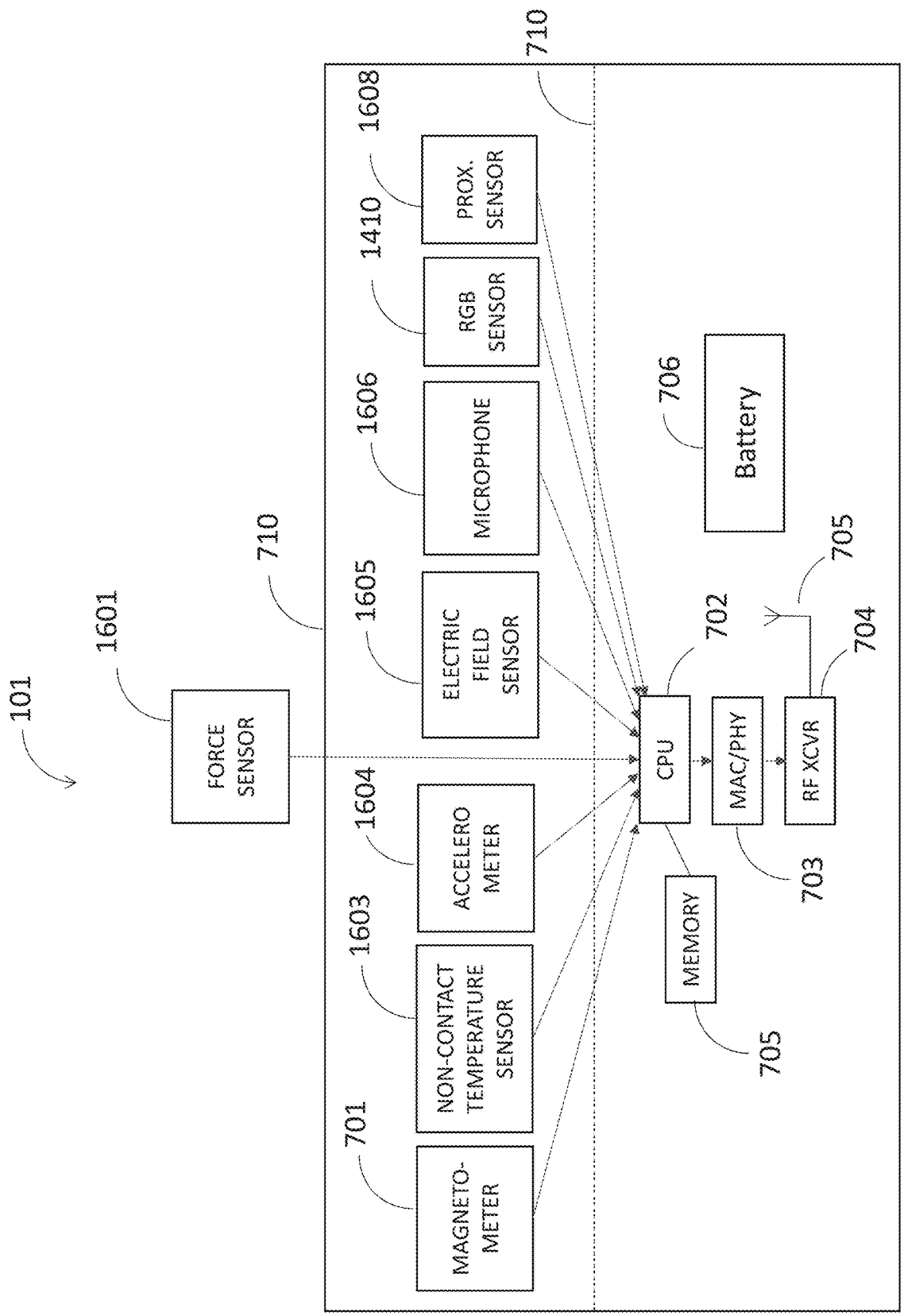
FIG. 16 shows a block diagram of a UCLS tag equipped with a magnetometer, an accelerometer, and several additional sensors, according to an example embodiment.

Turning now to FIG. 16, an alternative embodiment of UCLS tag 101 equipped with a magnetometer 701 and other sensors is shown. The other sensors include: a non-contact temperature sensor 1603, an accelerometer 1604, a force-sensitive resistor 1601, an electric field sensor 1605, a microphone 1606, an RGB color sensor 1410 and a proximity sensor 1608. The use of data from one or more of these other sensors in the feature vectors can be exploited to remove any overlap between in-use and not-in-use feature vector clusters and to generally improve detection performance by minimizing any chances of overlap between such clusters.

The non-contact temperature sensor 1603 could use an infrared thermopile to measure the temperature at a position on the host device by detecting the amount of IR radiation coming from the host device through a lens on the tag's enclosure 710. The non-contact temperature sensor 1603 could be used, for example, to detect usage when a patient is occupying a wheelchair or a bed, or sitting or standing in front of a computer screen, using a temperature at or near human body temperature to indicate usage. The non-contact temperature sensor 1603 could also be used to detect operational failures. For example, it could detect when a host device is overheating when measuring an unusually high operating temperature.

The accelerometer 1604 may be used to measure a vibration of the host device. To measure vibration, the accelerometer 1604 may be configured to provide uniformly spaced acceleration samples at 200 samples per second or higher. The amplitude and frequency content of the vibrations could be used to determine the usage state or condition of the host device.

Figure 17A:
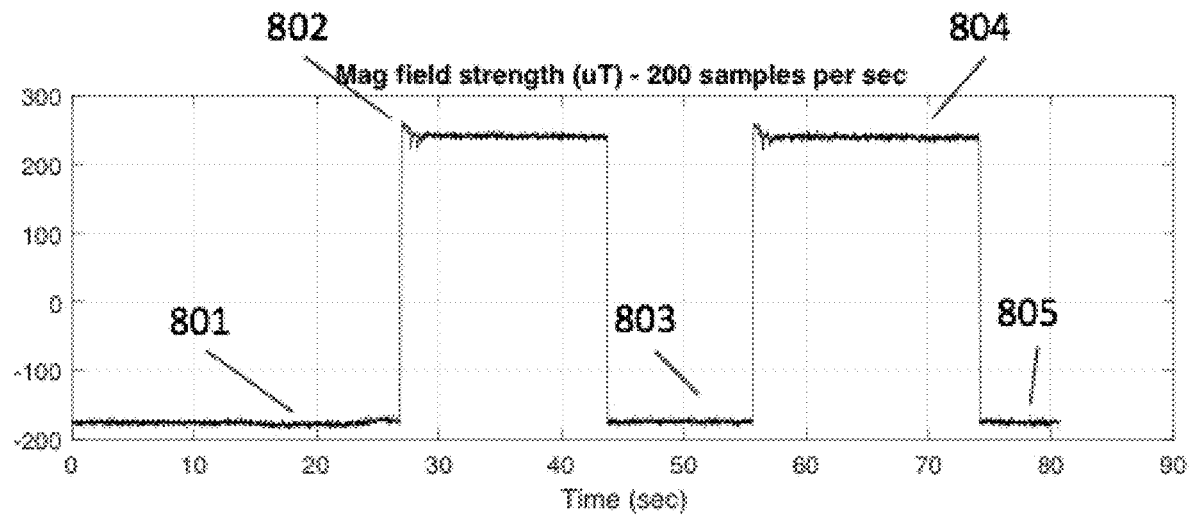
FIGS. 17a and 17b show magnetometer and accelerometer samples taken from a UCLS tag attached to a blood pressure monitor while the blood pressure monitor was turned on and off, according to an example embodiment.
Figure 17B:
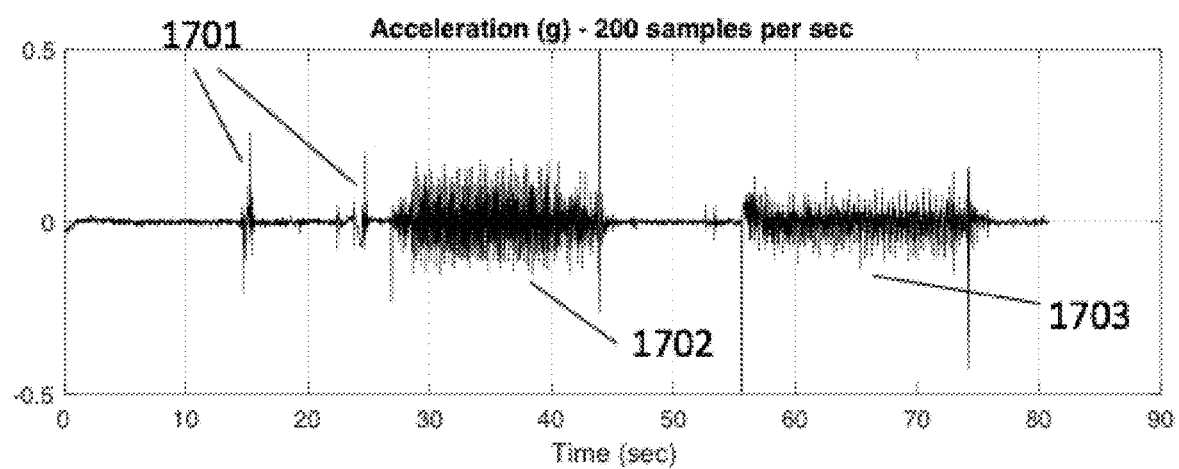

Reference is now made to FIGS. 17*a* and 17*b*, which show both magnetometer and accelerometer samples for the blood pressure monitor example from FIG. 8. FIG. 17*a* shows the same magnetometer samples 801-805 as displayed in FIG. 8. FIG. 17*b* shows the accelerometer samples taken simultaneously with the magnetometer data. The accelerometer measures acceleration in g and, like the magnetometer, is sampled at 200 kHz for this measurement. The spikes 1701 show when the button was pressed on the blood pressure monitor to start the measurement. Segments 1702 and 1703 clearly show vibrational activity while the DC motor is energized, as seen in segments 802 and 804.

Figure 18A:
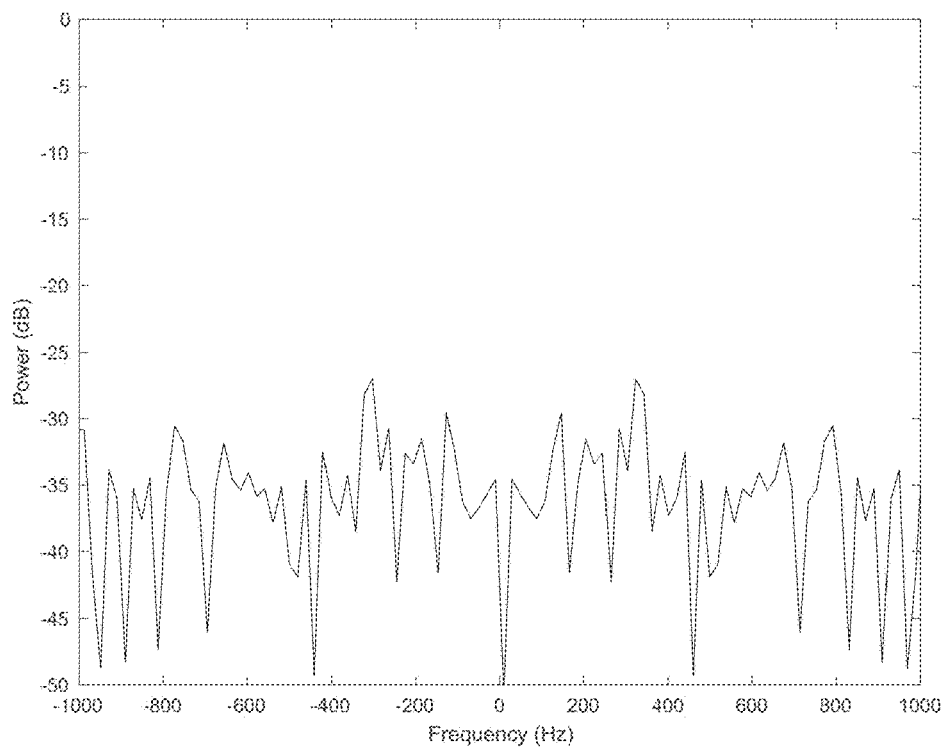
FIGS. 18a and 18b show frequency spectrum plots of the accelerometer samples from FIGS. 17a and 17b when the blood pressure monitor was actively being used and not actively being used, according to an example embodiment.
Figure 18B:
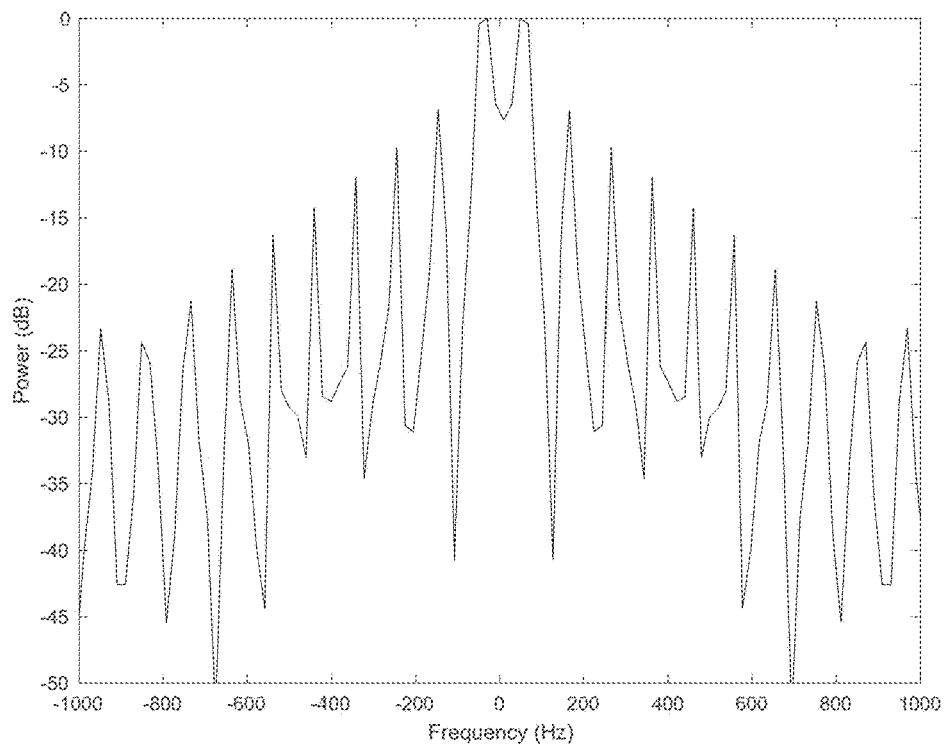

Turning now to FIGS. 18*a* and 18*b*, two frequency domain plots of the accelerometer samples from the blood pressure monitor experiment of FIGS. 17*a* and 17*b* are shown. Two 512-point FFTs were used to estimate the power-spectral density (PSD) of the accelerometer output. The PSD estimate shown in FIG. 18*a* was computed during a time when the blood pressure monitor was powered on but not pumping air—such as just before spike 1701 in FIG. 17*b*. The PSD estimate shown in FIG. 18*b* was computed in the middle of segment 1702, while the monitor was actively pumping air. FIG. 18*b* clearly shows a harmonic spectrum, indicative of a periodic vibration at a fundamental frequency of 54 Hz. FIG. 18*a* shows low-level white noise.

As shown in FIGS. 17*a*, 17*b*, 18*a* and 18*b*, the accelerometer could be used to detect when a host device is actively being used by looking for periodic vibrations at harmonics of some frequency in the known operating range of the host device. The relative amplitudes of the harmonics may be used as an additional check to confirm the in-use classification. The accelerometer may also be used to detect operational abnormalities of the host device by looking for significant changes in the fundamental frequency, amplitude, direction (if a 3-axis accelerometer is used) or frequency spectrum (i.e., the relative amplitudes of the harmonics) of the measured vibrations relative to a baseline range of values. The accelerometer may also predict operational abnormalities by looking for rapid deceleration in a particular direction—this would occur if the host device is dropped on the floor or slams into a wall. The same techniques may be used to detect usage activity or operating abnormalities on other motorized host devices that exhibit harmonic vibrations, such as ventilators (which vibrate at the breathing rate), centrifuges (which vibrate at their spin rate), beds (which use DC motors to pressurize air compartments), and infusion pumps (syringe pumps vibrate at the revolution rate of a screw driving the syringe; peristaltic pumps vibrate at the rotation rate of a motor pushing fluid through a tube).

Referring back to FIG. 16, the force sensor 1601 could be implemented using a force-sensitive resistor—a material which changes its resistance when a force or pressure is applied. It could be attached, for example, underneath, inside or on top of a hospital bed mattress or wheelchair cushion to determine when it's being used (occupied) by a patient. A force-sensitive resistor could attach to the UCLS tag 101 via a thin cable with 2 terminals. The CPU could detect the resistance by sourcing a known current into one terminal and digitizing the voltage on both terminals using an analog-to-digital converter (ADC). Such ADCs are embedded in many off-the-shelf CPU ICs. The measured resistance can then be found by dividing the difference in measured voltages by the known current. In addition to force-sensitive resistors—other force sensor implementations are also possible.

The electric field sensor 1605 could be used to detect electromagnetic interference (EMI) radiating from the host device in the form of electric fields. EMI that radiates from the host device in the form of magnetic fields would be picked up by the magnetometer 701, as discussed earlier. All electronic devices emit some level of EMI, and generally emit different patterns of EMI based on their operating state. For example, a ventilator could output a specific sequence of EMI emissions once per breathing interval while it depresses the piston used to deliver air to a patient. The time, duration, frequency content and sequence of emissions could be used to determine the usage state and/or condition of the host device. The electric field sensor 1605 could be implemented using an antenna of appropriate size and dimension given the frequencies being considered and the distance to the host-device electronics, followed by one or more amplifiers, followed by an analog-to-digital converter (ADC). When the ADC is digitized at a uniform sampling rate (e.g., 10 MHz), the EMI activity will appear as voltage fluctuations in the ADC sample stream. A rudimentary example of an electric field sensor 1605 that is widely used today is a handheld electric field sensor that is used to detect 120/220 VAC in an AC mains.

An alternative implementation for the electric field sensor 1605 that could be used to detect higher frequency signals is an antenna, followed by a low-noise amplifier, followed by a tunable RF downconverter, followed by a lowpass filter, followed by an ADC. The use of the downconverter would allow for the detection of arbitrarily high frequency signals by sweep-tuning the downconversion frequency.

The antenna at the input of the electric field sensor 1605 could be implemented using a PCB trace antenna, a chip antenna, or an external antenna attached to the UCLS tag PCB using a short cable. In some cases it could be preferable to use a so-called "near-field antenna", as these antennas tend to detect signals radiated very close to (typically within inches of) the antenna, while rejecting other signals. The electric near field could be detected using a short dipole, implemented, for example, by exposing a quarter-inch length of the inner conductor of an RF coax cable, and using the braided shield of the coax as the antenna ground.

The microphone 1606 could be used to determine usage or condition by monitoring the sound waves coming from the host device. Any host device that makes an identifiable audible sound when in use can be used as a candidate for usage detection via the microphone. For example, ventilators, blood pressure monitors, and centrifuges all make identifiable sounds when actively being used. These sounds can be characterized and identified by their audio spectrum using fast Fourier transforms (FFTs). The spectrum of the expected audio signal can be stored in a non-volatile memory on the tag, and a spectrum mask test can be used to determine whether it is actively being used. Alternatively, a harmonic analysis can be done on one or more of the FFTs to determine if the audio signal contains one or more periodic components, and if so, what the overall signal level of each component and is as well as the relative weighting of its harmonics.

The microphone 1606 could also be used to monitor the usage and condition of ultrasonic imaging equipment by looking for their periodic pulses of ultrasonic emissions. Sound waves can also be used to detect malfunctions in a host device. For example, the centrifuge rotation rate or audio frequency spectrum might change if it is not working properly. The acoustic frequency spectrum for an ultrasound machine could be an indicator for a malfunction.

The RGB color sensor 1410 was described above as a way to obtain ground truth information about the usage state of the host device by monitoring an LED 1407 on the host device through a light pipe 1408. This same approach could be used to determine the host device usage state in a more permanent way, i.e., as part of a monitoring procedure. The disadvantage of using this approach for monitoring is that in many cases, the use of a light pipe covering the front screen of a host device could be distracting to a user and aesthetically unpleasing.

The proximity sensor 1608 could be used to measure the presence of a human—for example, in a bed, a wheelchair, in front of an ultrasound or X-ray machine, etc. This information can be used to help determine whether a host device is being used. Small, low-cost proximity sensors can be found in smartphones and laptop PCs, and soap dispensers for handwashing, and the like. They typically use time-of-flight measurements with lasers or ultrasound emissions to measure proximity.

Any of the sensors shown in FIG. 16 can be located either inside the tag enclosure or outside. The one exception to this is the force sensor 1601, which in most cases will be located outside the tag. If all sensors other than the force sensor 1601 are located inside the tag 101, plastic enclosure (boundary) 710 would be used to represent the tag enclosure in FIG. 16. If all sensors are located outside the tag enclosure, boundary 710' would be used. It should be noted that any sensors located external to the tag 101 can either be directly connected to the tag PCB using a cable, or wirelessly connected using a wireless protocol such as Bluetooth™.

Figure 19:
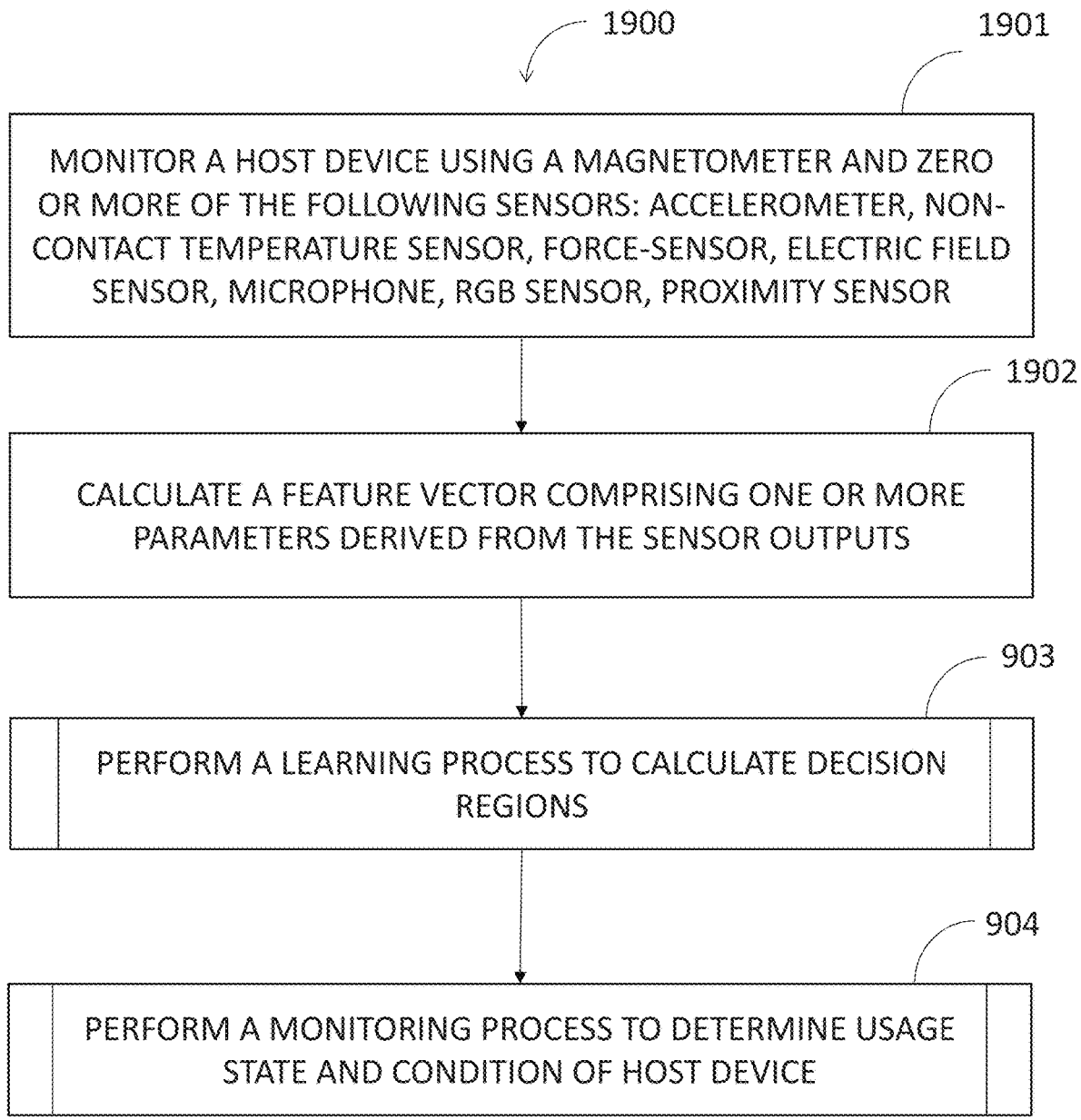
FIG. 19 illustrates a method for learning a host device's operating characteristics and monitoring the host device for usage or condition changes using a UCLS tag equipped with a magnetometer and possibly other sensors, according to an example embodiment.

Turning now to FIG. 19, a flow chart of a more generalized procedure 1900 for UCLS learning and monitoring is shown that supports the use of other sensors in addition to magnetometer 701 in the UCLS tags 101. The use of additional sensors improves detection performance (which can be quantified, for example, by measuring mean detection time for usage or condition state vs. false alarm rate) for most host devices by eliminating overlap between, and/or increasing the distance between, in-use and not-in-use feature vector clusters. Using both a magnetometer and an accelerometer to determine when the blood pressure monitor of FIGS. 8, 17a, and 17b is being used will perform at least as well as the accelerometer only. For certain host devices such as wheel chairs, additional sensors are required. For example, for a wheel chair, the magnetometer of the UCLS tag 101 could be disabled (since it does not provide any meaningful information as to the wheel chair's occupancy), and one or more of the force-sensitive resistor 1601, non-contact temperature sensor 1603 or proximity sensor 1608 could be used to detect its occupancy.

The procedure 1900 is identical to the learning and monitoring method/procedure 900 of FIG. 9, described above, except operations 1901 and 1902 replace operations 901 and 902. The operations 1901 and 1902 allow for the possibility of using other sensors in addition to the magnetometer. The learning process 903 and monitoring process 904 remain unchanged and continue to be used in procedure 1900. At 1901, a device such as a UCLS tag 101 uses a magnetometer and zero or more of the following sensors to monitor a host device: accelerometer, non-contact temperature sensor, force-sensitive resistor, electromagnetic interface (EMI) detector, microphone, RGB sensor, proximity sensor. At 1902, feature vectors based on the magnetometer and zero or more sensor outputs are calculated. The additional feature vector components based on the additional sensors could include: (1) mean, maximum, minimum, median, RMS, fundamental frequency, primary and secondary fundamental frequencies, energy content of primary and secondary fundamental frequencies and harmonics thereof, spectral envelope, period or duty cycle, peak☐to☐Q average power of magnetometer, accelerometer, electric field sensor or microphone samples; (2) light intensity at R, G and B frequencies from RGB sensor; (3) force-sensitive resistor resistance measurement; (4) proximity indication from proximity sensor; or (5) temperature reading from non-contact temperature sensor.

Referring back to FIG. 11, the HDCP procedure 1100 also needs minor modifications to support multiple sensors. At 1101, instead of streaming only magnetometer samples to the smartphone or PC application, the samples from all relevant sensors should be sent instead. In step 1104, the App should buffer and store not only the magnetometer samples, but samples from all relevant sensors instead.

Figure 20:
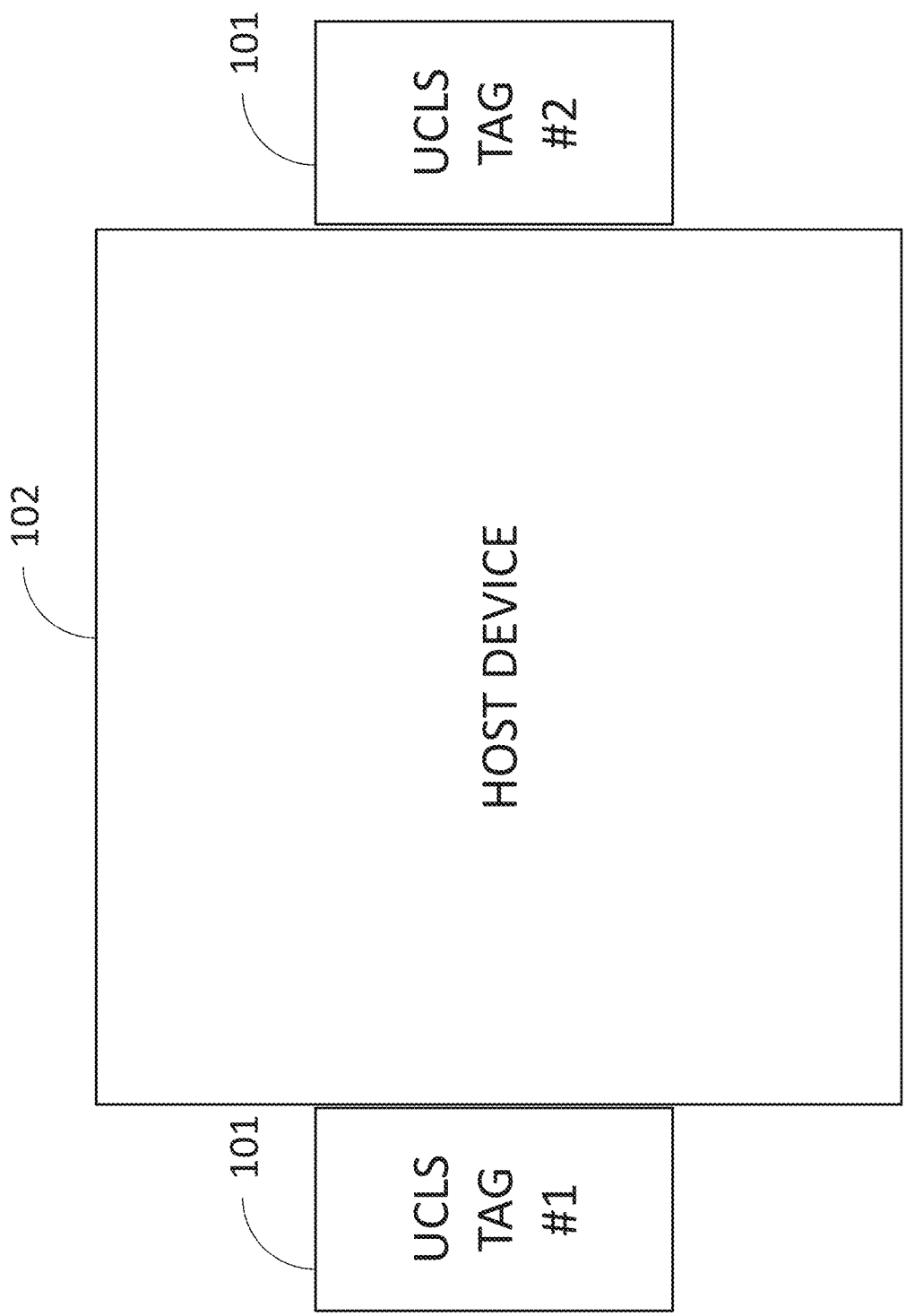
FIG. 20 illustrates how multiple UCLS tags can be used to monitor a host device, according to an example embodiment.

Turning to FIG. 20, for certain host devices, the optimal location for sensing activity of the device 102 can be in different locations on the enclosure of the device 102. For example, one location can be optimal for detecting vibration of a motor, while a second location is optimal for detecting electrical activity associated with a CPU board. For these devices, multiple UCLS tags 101 may be affixed to the different locations on the enclosure. The sensor data collected from the multiple UCLS tags 101 may be combined (at the UCLS server 105) to determine the final operating state or condition of the device 102, such as a medical device. Alternatively, the UCLS tags 101 may share sensor data with each other using their Bluetooth Low Energy (BLE) radios, such that operating state and condition determination may be made locally at one of the UCLS tags 101.

Figure 21:
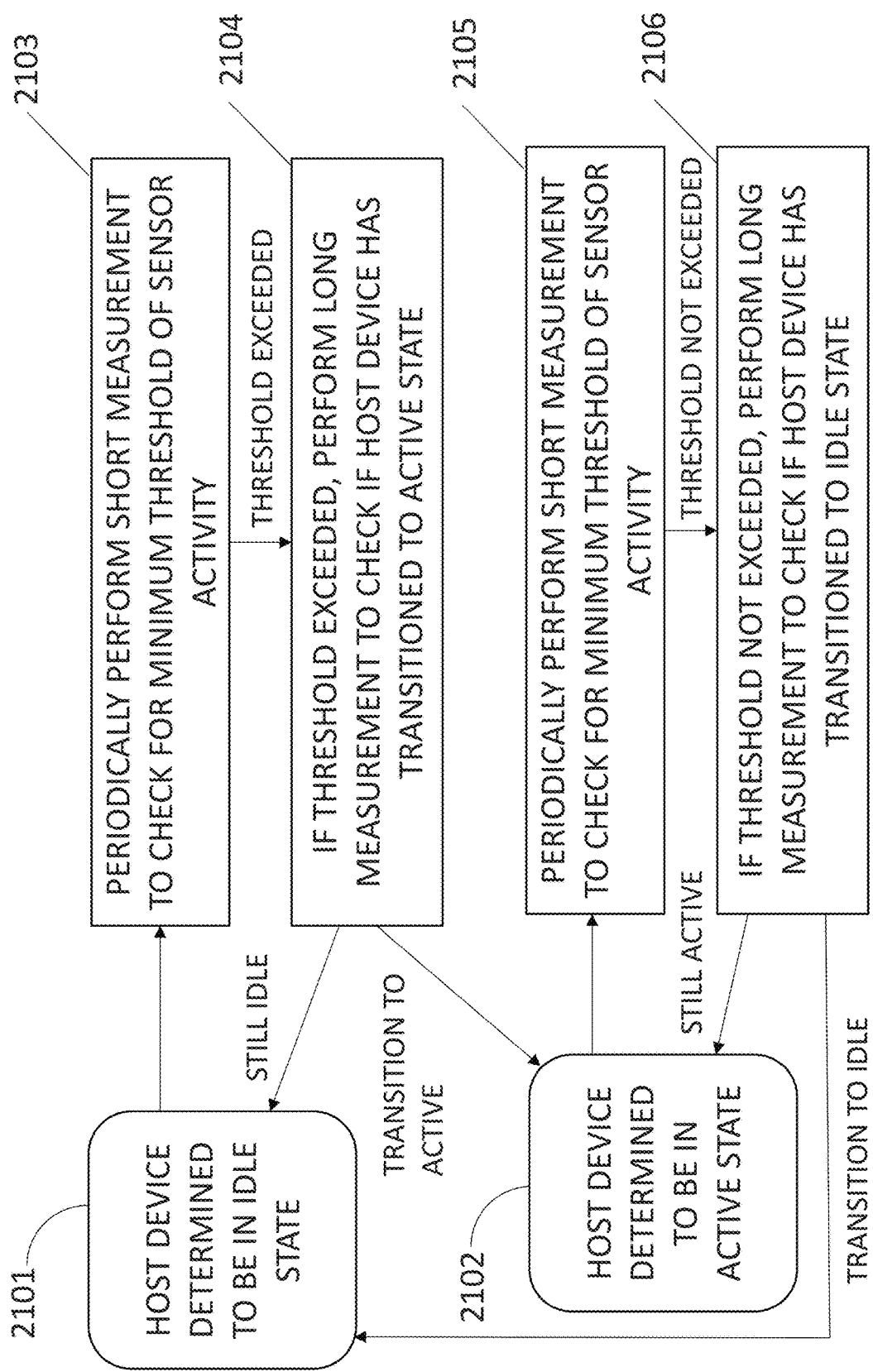
FIG. 21 illustrates a flow chart depicting a procedure for using short and long measurement intervals on a UCLS tag to monitor a host device's usage or condition activity in order to maximize the UCLS tag's battery life, according to an example embodiment.

Reference is now made to FIG. 21. The UCLS tag may detect changes in the usage state of an attached medical device in a manner that maximizes the battery life of the tag. To maximize the battery life, the UCLS tag software implements a state machine that allows the tag to only enable sensors and process sensor data for the minimum amounts of time. When the host device is currently determined to be in "Idle" state 2101, the UCLS tag periodically (such as once every 30 seconds) performs a short measurement (such as 10 milliseconds) 2103 to determine whether there is any activity on a particular sensor (such as vibration) above a threshold. If the short measurement does not show activity above the threshold, then the UCLS tag goes to sleep until the next measurement interval. If the short measurement does show activity above the threshold, then the UCLS tag will perform a longer measurement (such as 3 seconds) 2104 to determine whether the sensor readings match the criteria necessary to transition the host device usage to "Active" state 2102. Similarly, when the host device is currently determined to be in "Active" state 2102, the UCLS tag will periodically (such as every 30 seconds) perform a short measurement (10 milliseconds) 2105 to determine whether there continues to be activity on a particular sensor (vibration) above a threshold. If that short measurement does show activity above the threshold, then the tag goes to sleep until the next measurement interval. If that short measurements does not show activity above the threshold, then the UCLS tag performs a longer measurement (3 seconds) 2106 to determine whether the sensor readings no longer match the "Active State" criteria, and if they do not it will transition the host device usage to "Idle" state 2101.

Figure 22:
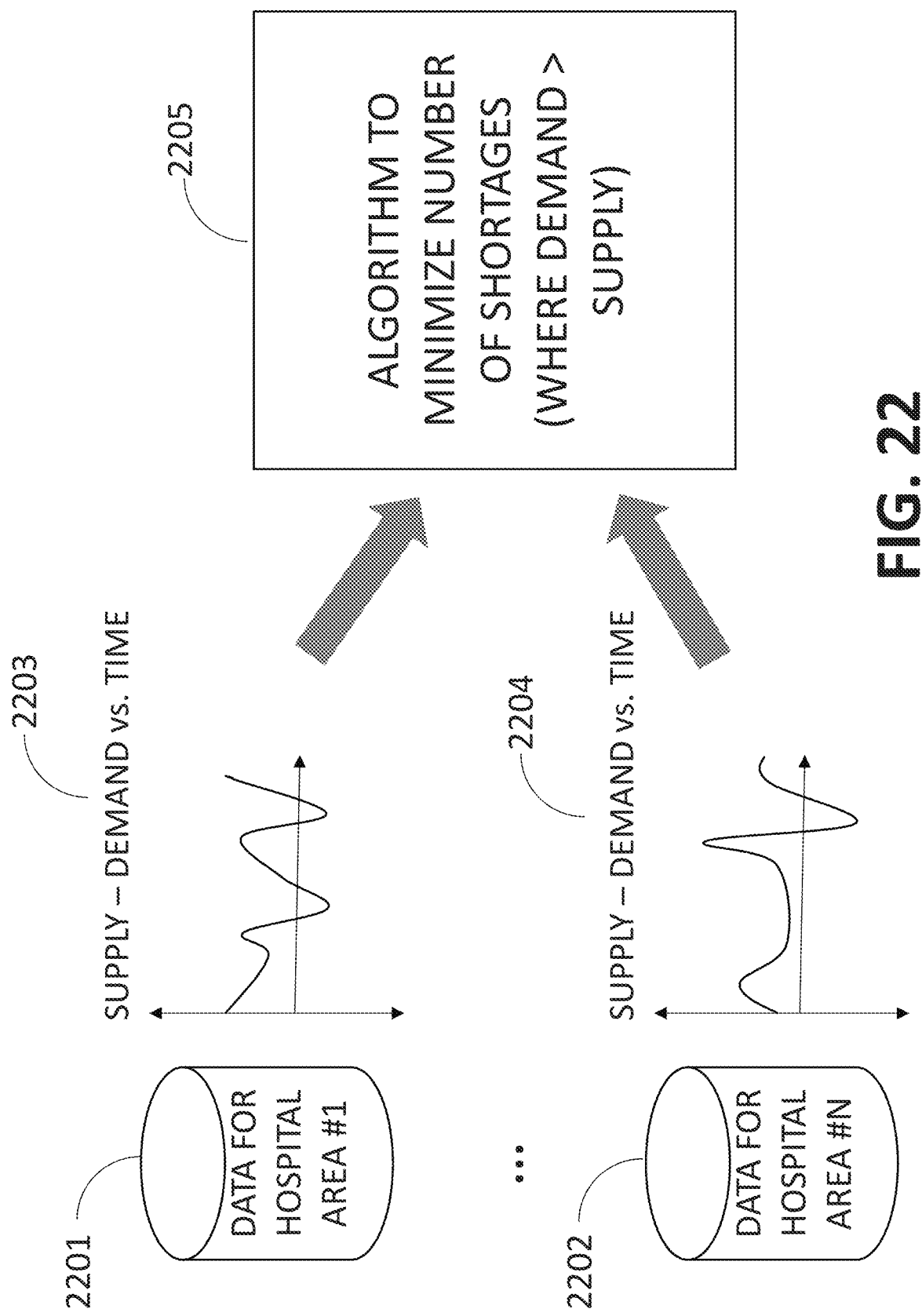
FIG. 22 illustrates a method for minimizing the number of supply shortages of a group of host devices of a particular type in a working environment, according to an example embodiment.

Reference is now made to FIG. 22. The UCLS server 105 collects utilization and location data vs. time for each medical device. The data is sub-divided into different areas of the hospital (2201, 2202), for example an area may be a specific floor and wing associated with a hospital function such as Emergency Room, Post-Operative, etc. The server software running on the UCLS server 105 periodically (ex. once per month) runs an analysis of utilization for a specific medical device type to discover periods of time in which the available inventory for that device type in an area was 0 (or alternatively below some low-water threshold), as shown in 2203 and 2204. These periods of time represent instances where medical staff would not be able to find an available device of that type in that area. As such, these areas are identified as "low-availability" areas for that type of device. The UCLS server 105 also identifies any areas of the hospital where the available inventory for that device type is always high (above a high-water threshold). These areas are identified as "high-availability" areas for that type of device. Based on the list of high and low availability areas, the UCLS server 105 uses an optimization algorithm 2205 that makes recommendations to the hospital staff regarding relocating a number of medical assets from high-availability to a low-availability areas. If no high-availability areas exist, the UCLS server 105 uses an optimization algorithm 2205 that makes recommendations to the hospital staff regarding acquiring addition equipment and allocating the equipment to the low-availability areas.

Figure 23:
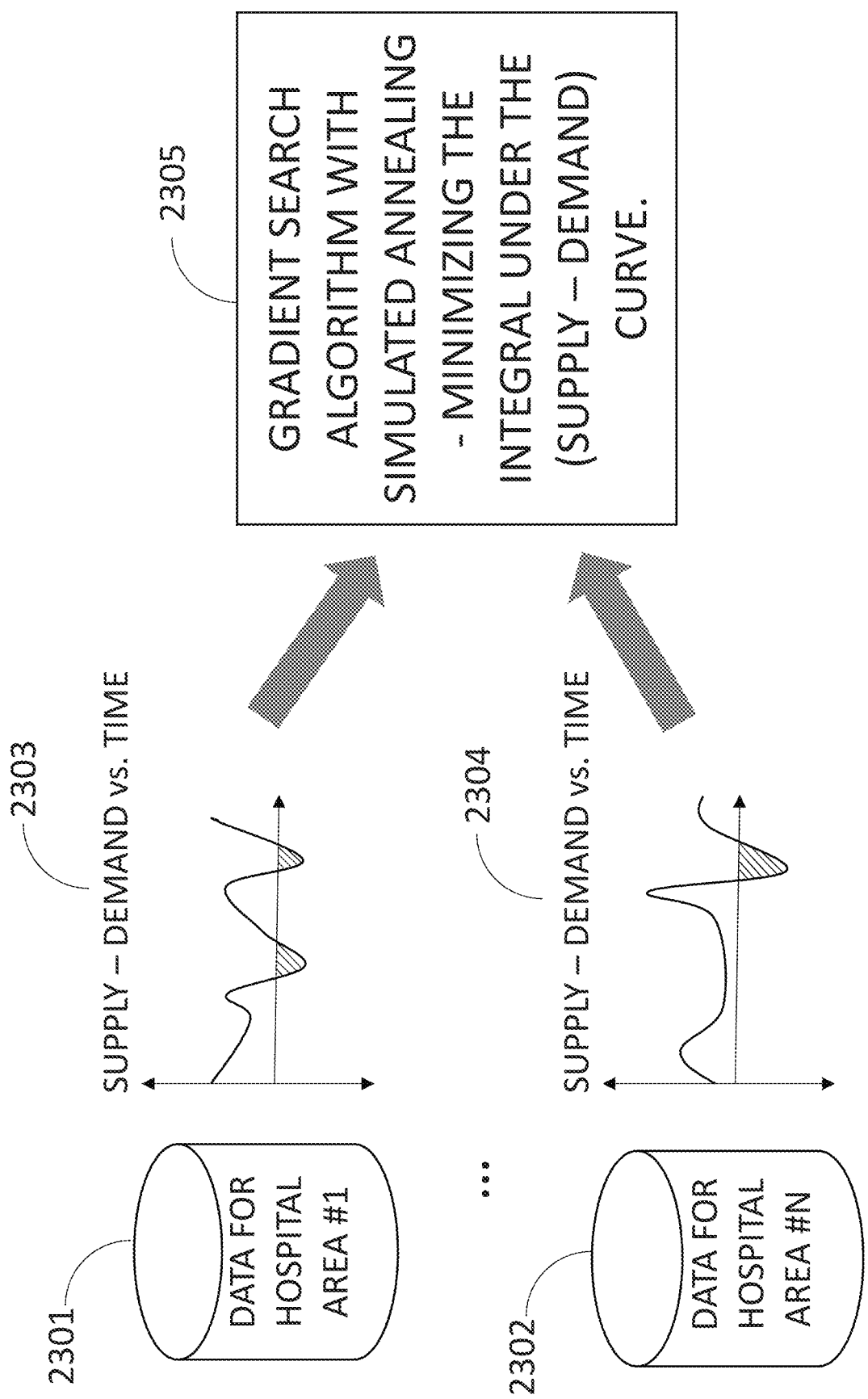
FIG. 23 illustrates a method for using a gradient search with simulated annealing to find an optimum allocation of a group of host devices of a particular type in a working environment, according to an example embodiment.

A specific approach that can be applied to the optimization problem described above is Gradient Search with Simulated Annealing, as shown in FIG. 23. The goal of the server optimization algorithm is to search across all possible allocations of devices to areas of the hospital in order to minimize a cost function. Data 2301 and 2302 and thresholds 2303 and 2304 are similar to that described above in connection with FIG. 22. The cost function is defined as the area under the available supply curve where supply falls below a minimum availability threshold (2303 and 2304). Since the search space can be large, exhaustive search may not be possible. As such, a Gradient Search approach is applied (2305), which follows consecutive small changes that result in increasingly better cost functions. But because Gradient Search techniques are subject to finding "local" rather than "global" maximums, a Simulated Annealing approach is added to reduce the issue of local maximums. In the Simulated Annealing approach, larger jumps in allocation are periodically attempted to see if they result in a better search path.

Artificial Neural Networks

An alternative to using clustering methods for usage and condition state detection would be to use an artificial neural network (ANN). Instead of using decision regions to determine usage state from a feature vector, an ANN-based implementation would process each feature vector using an array of neurons that would combine to produce a usage state and condition state estimate. Ground truth information could be used to train the ANN by adjusting the weights used to combine the neurons in order to minimize some appropriate cost function—e.g., minimum mean-squared error against ground truth.

Led Sensor Probe

Figure 24:
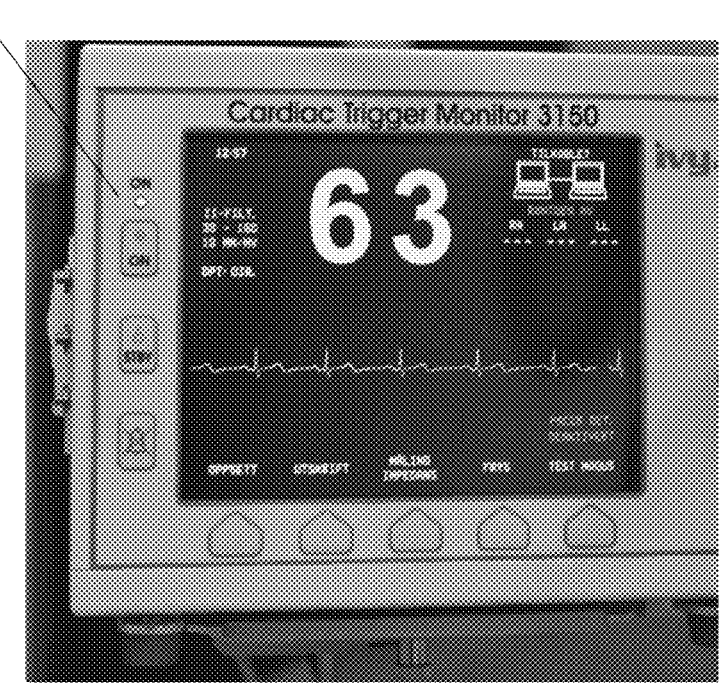
FIG. 24 shows an example host device with an LED on the front-panel that can be used to detect the usage state of the host device, according to an example embodiment.
Figure 25:
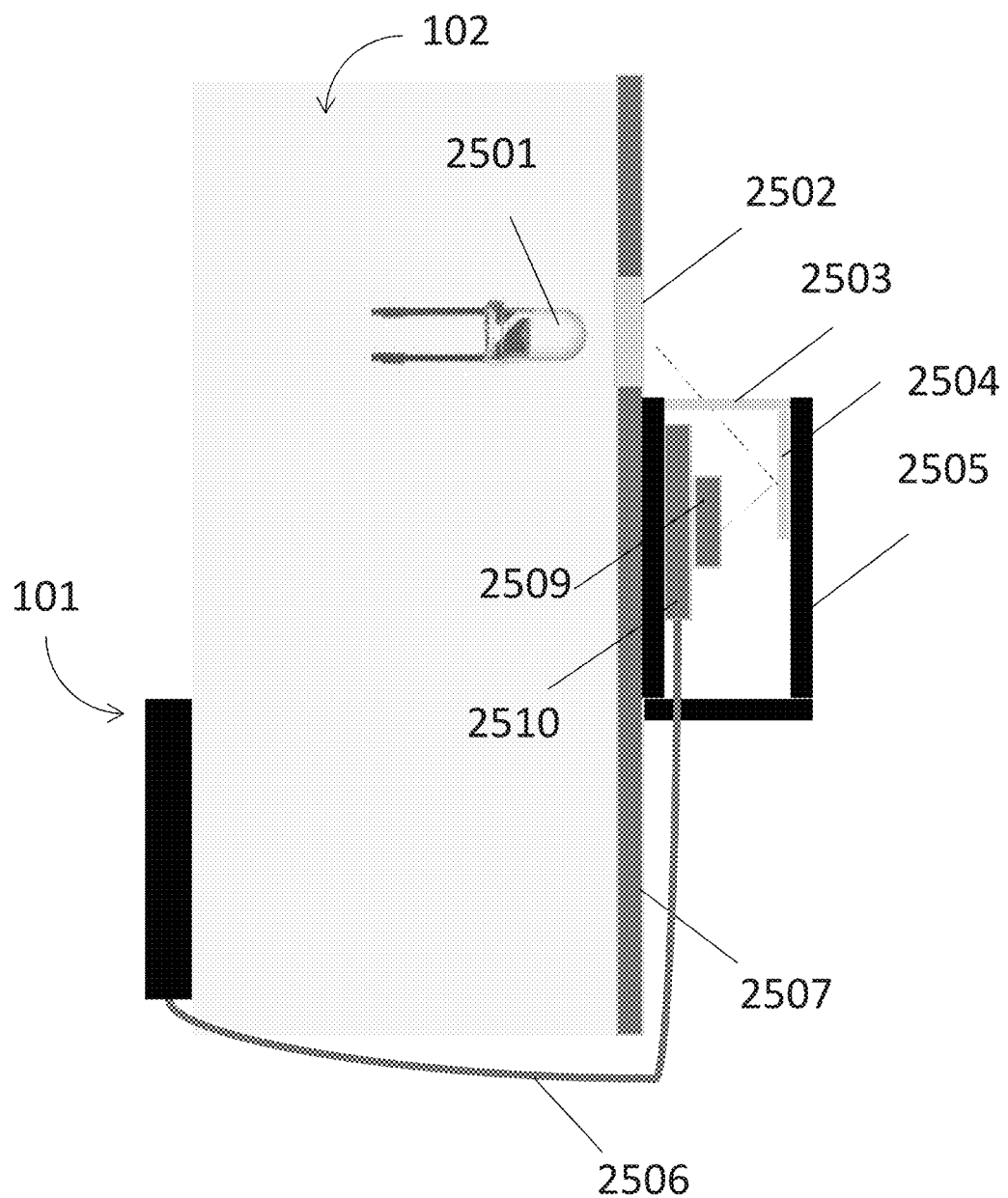
FIG. 25 shows an LED sensor probe apparatus that can be used to detect the color and intensity of an LED on a host device front panel in order to determine the usage state of the host device, according to an example embodiment.

Reference is now made to FIG. 24, which shows the user interface of a cardiac monitor. The on/off LED 2401 is an example of an LED that could be monitored using a light pipe and RGB color sensor mounted in the UCLS tag 101, as described above. Turning now to FIG. 25, an alternative approach for monitoring the LED is illustrated. FIG. 25 shows a cross-sectional view of a host device 102 with the front panel screen 2507 aiming toward the right side of the page. An LED 2501 behind the front panel shines light through a transparent or translucent protective LED lens 2502. An LED sensor probe assembly 2505 could be placed next to the lens 2502 to monitor the LED 2501. Light from the LED 2501 comes through the lens 2502, passes through a second transparent or translucent protective lens 2503 on the sensor probe assembly 2505, reflects off of a reflective surface 2504 inside the sensor probe assembly 2505, and then hits RGB color sensor 2509. The RGB color sensor 2509 may be mounted on a printed circuit board 2510 inside the sensor probe assembly 2505. The digital red, green, blue and white color intensity measurements output from the RGB sensor 2509 may be sent via a cable 2506 to a UCLS tag 101 mounted on the back of the host device 102, where the UCSL tag will minimize user distraction. Using modern surface mount electrical components, the physical dimensions of the sensor probe assembly 2505 may be made to be very small—e.g., 3×3×2 mm. Both the small size of sensor probe assembly 2505 and the fact that it is mounted next to (but not on top of) LED lens 2502 on the host device 102 also help to minimize user distraction.

Figure 26:
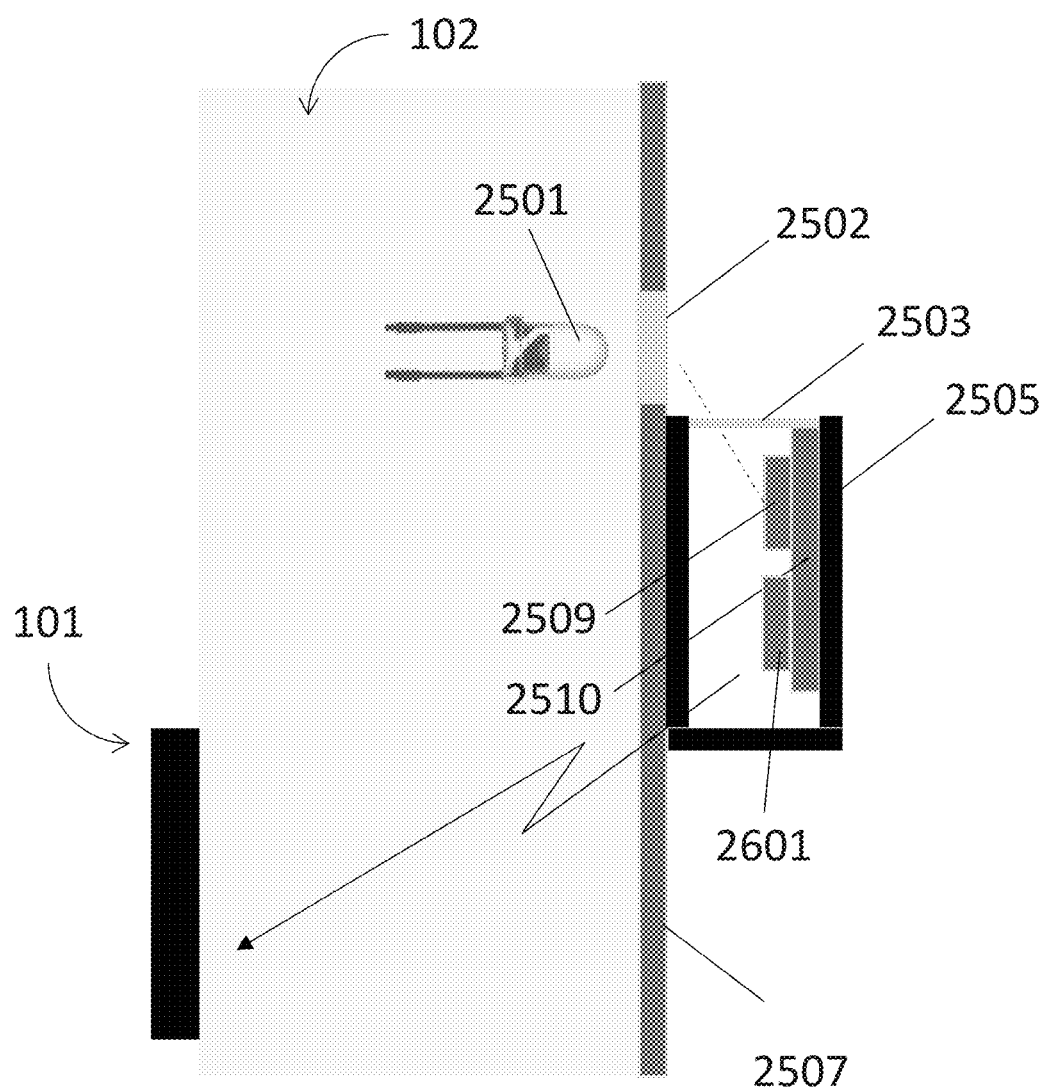
FIG. 26 shows an alternative implementation of an LED sensor probe apparatus that can be used to detect the color and intensity of an LED on a host device front panel in order to determine the usage state of the host device, according to an example embodiment.

Turning now to FIG. 26, an alternative implementation for the LED sensor probe assembly 2505 is shown. Instead of using reflective surface 2504 to reflect the LED image onto the RGB sensor 2509, the printed circuit board 2510 and RGB sensor 2509 are located on the far side of the sensor probe assembly 2505, with the RGB sensor 2509 facing the LED 2501 and lens 2502. Also, instead of using cable 2506 to pass the RGB color sensor measurements from the sensor probe assembly 2505 to the UCLS tag 101, the measurements could be transmitted wirelessly using an integrated wireless transceiver 2601 such as a Bluetooth 5™ module with a chip antenna. This would require a small battery to be used in the probe, which is not shown in FIG. 26. The removal of the cable 2506 in this implementation may make it less intrusive or distracting, and therefore more palatable for a user.

Figure 27:
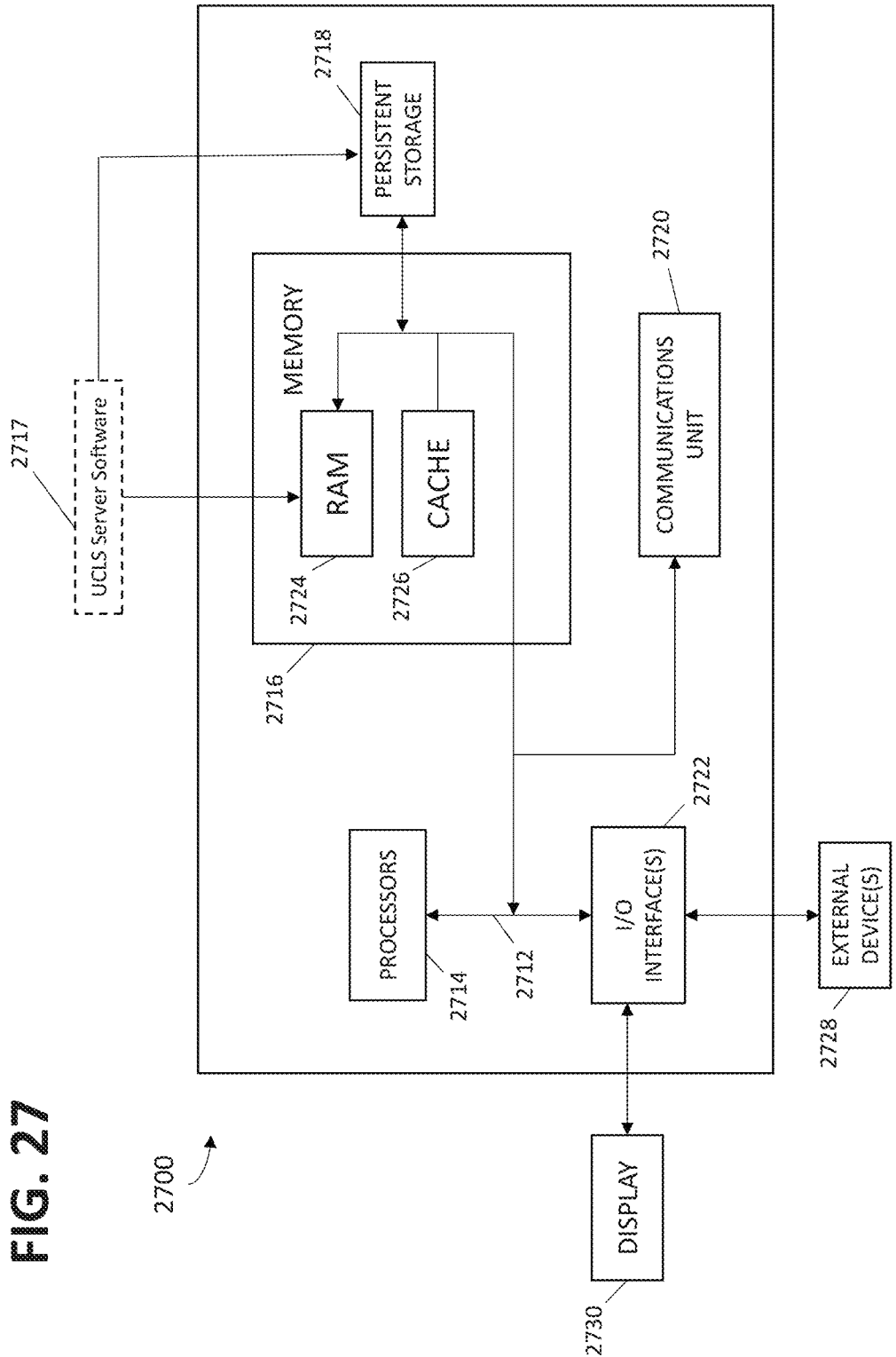
FIG. 27 illustrates a block diagram of a computing device that may be configured to perform the operations of a UCLS server, according to an example embodiment.

FIG. 27 illustrates a hardware block diagram of a computing device 2700 that may perform the functions of any of the computing entities referred to herein, such as the UCLS server 105. It should be appreciated that FIG. 27 provides only an illustration of one embodiment and does not imply any limitations with regard to the environments in which different embodiments may be implemented. Many modifications to the depicted environment may be made.

As depicted, the device 2700 includes a bus 2712, which provides communications between computer processor(s)

2714, memory 2716, persistent storage 2718, communications unit 2720, and input/output (I/O) interface(s) 2722. Bus 2712 can be implemented with any architecture designed for passing data and/or control information between processors (such as microprocessors, communications and network processors, etc.), system memory, peripheral devices, and any other hardware components within a system. For example, bus 2712 can be implemented with one or more buses.

Memory 2716 and persistent storage 2718 are computer readable storage media. In the depicted embodiment, memory 2716 includes random access memory (RAM) 2724 and cache memory 2726. In general, memory 2716 can include any suitable volatile or non-volatile computer readable storage media. Instructions for the UCLS server software 2717 may be stored in memory 2716 or persistent storage 2718 for execution by processor(s) 2714.

One or more programs may be stored in persistent storage 2718 for execution by one or more of the respective computer processors 2714 via one or more memories of memory 2716. The persistent storage 2718 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 2718 may also be removable. For example, a removable hard drive may be used for persistent storage 2718. Other examples include optical and magnetic disks, thumb drives, and smart cards that are inserted into a drive for transfer onto another computer readable storage medium that is also part of persistent storage 2718.

Communications unit 2720, in these examples, provides for communications with other data processing systems or devices. In these examples, communications unit 2720 includes one or more network interface cards. Communications unit 2720 may provide communications through the use of either or both physical and wireless communications links.

I/O interface(s) 2722 allows for input and output of data with other devices that may be connected to computer device 2700. For example, I/O interface 2722 may provide a connection to external devices 2728 such as a keyboard, keypad, a touch screen, and/or some other suitable input device. External devices 2728 can also include portable computer readable storage media such as database systems, thumb drives, portable optical or magnetic disks, and memory cards.

Software and data used to practice embodiments can be stored on such portable computer readable storage media and can be loaded onto persistent storage 2718 via I/O interface(s) 2722. I/O interface(s) 2722 may also connect to a display 2730. Display 2730 provides a mechanism to display data to a user and may be, for example, a computer monitor.

The programs described herein are identified based upon the application for which they are implemented in a specific embodiment. However, it should be appreciated that any particular program nomenclature herein is used merely for convenience, and thus the embodiments should not be limited to use solely in any specific application identified and/or implied by such nomenclature.

Data relating to operations described herein may be stored within any conventional or other data structures (e.g., files, arrays, lists, stacks, queues, records, etc.) and may be stored in any desired storage unit (e.g., database, data or other repositories, queue, etc.). The data transmitted between entities may include any desired format and arrangement, and may include any quantity of any types of fields of any size to store the data. The definition and data model for any datasets may indicate the overall structure in any desired fashion (e.g., computer-related languages, graphical representation, listing, etc.).

The present embodiments may employ any number of any type of user interface (e.g., Graphical User Interface (GUI), command-line, prompt, etc.) for obtaining or providing information (e.g., data relating to scraping network sites), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The environment of the present embodiments may include any number of computer or other processing systems (e.g., client or end-user systems, server systems, etc.) and databases or other repositories arranged in any desired fashion, where the present embodiments may be applied to any desired type of computing environment (e.g., cloud computing, client-server, network computing, mainframe, stand-alone systems, etc.). The computer or other processing systems employed by the present embodiments may be implemented by any number of any personal or other type of computer or processing system (e.g., desktop, laptop, PDA, mobile devices, etc.), and may include any commercially available operating system and any combination of commercially available and custom software (e.g., machine learning software, etc.). These systems may include any types of monitors and input devices (e.g., keyboard, mouse, voice recognition, etc.) to enter and/or view information.

It is to be understood that the software of the present embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present embodiments may alternatively be implemented by any type of hardware and/or other processing circuitry.

Each of the elements described herein may couple to and/or interact with one another through interfaces and/or through any other suitable connection (wired or wireless) that provides a viable pathway for communications. Interconnections, interfaces, and variations thereof discussed herein may be utilized to provide connections among elements in a system and/or may be utilized to provide communications, interactions, operations, etc. among elements that may be directly or indirectly connected in the system. Any combination of interfaces can be provided for elements described herein in order to facilitate operations as discussed for various embodiments described herein.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The embodiments presented may be in various forms, such as a system, a method, and/or a computer program product at any possible technical detail level of integration. The computer program product may include a computer readable storage medium (or media) having computer readable program instructions thereon for causing a processor to carry out aspects of presented herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present embodiments may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Python, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects presented herein.

Aspects of the present embodiments are described herein with reference to flowchart illustrations and/or block diagrams of methods, apparatus (systems), and computer program products according to the embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In one form, a usage, condition and location system (UCLS) tag is provided, comprising; a magnetometer or a connection to an external magnetometer configured to provide a measurement of magnetic field activity emanating from electronics contained within a host device to which the tag or external magnetometer is attached; zero or more additional sensors or a connection to zero or more additional sensors which are external to the tag, the zero or more additional sensors including: a contactless temperature sensor configured to provide a temperature measurement of the host device or of a user of the host device; a force sensor configured to provide a weight measurement of a user of the host device; an accelerometer configured to provide an acceleration measurement of the host device; an electric field sensor configured to provide a measurement of electric field activity emanating from the electronics contained within the host device; a microphone configured to provide a sound measurement associated with sounds emitted from the host device; a color sensor, configured to provide intensity and color measurements of a light source on the host device; and a proximity sensor, configured to provide a proximity indication of whether a user is on or near the host device; a processor configured to: calculate a feature vector comprising one or more parameters derived from the magnetometer and the zero or more additional sensors; accumulate feature vectors over a period of time; determine whether the feature vector or a statistic derived from the accumulated feature vectors occupies one or more of a set of decision regions; and if the feature vector or statistic occupies one or more of the decision regions, determine a current usage state of the host device based on the decision region or regions occupied by the feature vector or statistic and a learned usage state associated with the decision region or regions occupied by the feature vector or statistic; a wireless transceiver configured to transmit a data packet that includes information representing the current usage state; and an energy storage device configured to supply power to the magnetometer, the zero or more additional sensors, the processor and the wireless transceiver.

In another form, a method for determining a usage state and a condition of a host device is provided, comprising: monitoring a host device using sensor outputs obtained from a usage, condition and location system (UCLS) tag that includes a magnetometer and zero or more of an accelerometer, a non-contact temperature sensor, a force sensor, an electric field sensor, a microphone, a color sensor and a proximity sensor; calculating a feature vector comprising one or more parameters derived from the sensor outputs; performing a learning process that includes: accumulating a first set of feature vectors over a period of time; identifying clusters of feature vectors in the first set of feature vectors; calculating decision regions around each cluster; and associating a usage state of the host device with each of the clusters; performing a monitoring process that includes: accumulating a second set of feature vectors over a period of time; determining whether the feature vector or a statistic derived from the second set of feature vectors occupies one or more of the decision regions; and if the feature vector or statistic occupies one or more of the decision regions, determining a current usage state of the host device based on the decision region or regions occupied by the feature vector or statistic and the usage state associated with the cluster associated with the decision region or regions occupied by the feature vector or statistic.

In still another form, a usage, condition and location system (UCLS) is provided comprising; one or more UCLS tags, each tag comprising: a magnetometer or a connection to an external magnetometer configured to provide a measurement of magnetic field activity emanating from electronics contained within a host device to which the tag is attached; zero or more additional sensors or a connection to zero or more additional sensors which are external to tag, the zero or more additional sensors including: a contactless temperature sensor configured to provide a temperature measurement of the host device or of a user of the host device; a force sensor configured to provide a weight measurement associated with the host device; an accelerometer configured to provide an acceleration measurement of the host device; an electric field sensor configured to provide a measurement of electric field activity emanating from the electronics contained within the host device; a microphone configured to provide a sound measurement associated with sounds emitted from the host device; a color sensor, configured to provide intensity and color measurements of a light source on the host device; and a proximity sensor, configured to provide a proximity indication of whether a user is on or near the host device; a processor configured to: calculate a feature vector comprising one or more parameters derived from the magnetometer and the zero or more additional sensors; accumulate feature vectors over a period of time; determine whether the feature vector or a statistic derived from the accumulated feature vectors occupies one or more of a set of decision regions stored on the one or more UCLS tags; and if the feature vector or statistic occupies one or more of the decision regions, determine a current usage state of the host device based on the decision region or regions occupied by the feature vector or statistic and a learned usage state associated with the decision region or regions occupied by the feature vector or statistic; a wireless transceiver configured to transmit a data packet that includes information representing the current usage state; and an energy storage device configured to supply power to the magnetometer, the zero or more additional sensors, the processor and the wireless transceiver; a UCLS server; and one or more user terminals, wherein: the UCLS server determines the location of the one or more UCLS tags using data packets transmitted by the one or more UCLS tags; the UCLS server extracts one or more current usage states from the data packets transmitted by the one or more UCLS tags and stores the one or more current usage states in a database; and the one or more user terminals retrieve the current usage states from the database via the UCLS server and display the current usage states to one or more users.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A usage, condition and location system (UCLS) tag, comprising;
    a magnetometer or a connection to an external magnetometer configured to provide a measurement of magnetic field activity emanating from electronics contained within a host device to which the tag or external magnetometer is attached;
    one or more additional sensors or a connection to one or more additional sensors which are external to the tag, the one or more additional sensors including:
        a contactless temperature sensor configured to provide a temperature measurement of the host device or of a user of the host device;
        a force sensor configured to provide a weight measurement of a user of the host device;
        an accelerometer configured to provide an acceleration measurement of the host device;
        an electric field sensor configured to provide a measurement of electric field activity emanating from the electronics contained within the host device;
        a microphone configured to provide a sound measurement associated with sounds emitted from the host device;
        a color sensor, configured to provide intensity and color measurements of a light source on the host device; and
    a proximity sensor, configured to provide a proximity indication of whether a user is on or near the host device;
    a processor configured to:
        calculate a feature vector comprising one or more parameters derived from the magnetometer and the one or more additional sensors;
        accumulate feature vectors over a period of time to provide accumulated feature vectors;
        determine whether the feature vector or a statistic derived from the accumulated feature vectors occupies one or more of a set of decision regions; and
        if the feature vector or statistic occupies one or more of the decision regions, determine a current usage state of the host device based on the decision region or regions occupied by the feature vector or statistic and a learned usage state associated with the decision region or regions occupied by the feature vector or statistic;
    a wireless transceiver configured to transmit a data packet that includes information representing the current usage state; and
    an energy storage device configured to supply power to the magnetometer, the one or more additional sensors, the processor and the wireless transceiver.

2. The UCLS tag of claim 1, wherein the host device is a wheelchair or a bed, and wherein the feature vector includes a component based on the temperature measurement from the contactless temperature sensor, the proximity indication from the proximity sensor, or the weight measurement from the force sensor indicative of whether a hospital patient is occupying the wheelchair or bed.

3. The UCLS tag of claim 1, wherein the magnetometer, one or more additional sensors, processor, wireless transceiver and energy storage device are contained within an enclosure, the enclosure further including feet configured to make direct contact with the host device so as to minimize dampening of the acceleration measurement.

4. The UCLS tag of claim 1, wherein the wireless transceiver is configured to receive location information from a location beacon before transmitting the data packet, and wherein the processor is configured to include location information in the data packet.

5. The UCLS tag of claim 1, wherein the connection to the external magnetometer or the connection to the one or more additional sensors is a wireless connection.

6. The UCLS tag of claim 1, wherein the connection to the external magnetometer or the connection to one or more additional sensors is a wired connection.

7. The UCLS tag of claim 1, wherein the host device is powered from an AC mains, an internal battery, or both.

8. The UCLS tag of claim 1, wherein the UCLS tag, the external magnetometer, or one of the one or more additional sensors which are external to the tag is configured to be mounted to one of the following positions on the host device: on an enclosure of the host device; on a front or back of a display screen; on an enclosure of the host device proximate to an AC-to-DC converter and/or a DC power supply of the host device; on an enclosure of the host device, proximate to an electric motor; or on or proximate to a light-emitting diode (LED) on the host device.

9. The UCLS tag of claim 1, wherein the UCLS tag obtains information describing a definition of the feature vector, the set of decision regions and the learned usage state associated with each decision region from a database stored on a server.

10. A method for determining a usage state and a condition of a host device, comprising:
monitoring a host device using sensor outputs obtained from a usage, condition and location system (UCLS) tag that includes a magnetometer and one or more of an accelerometer, a non-contact temperature sensor, a force sensor, an electric field sensor, a microphone, a color sensor and a proximity sensor;
calculating a feature vector comprising one or more parameters derived from the sensor outputs;
performing a learning process that includes:
accumulating a first set of feature vectors over a period of time;
identifying clusters of feature vectors in the first set of feature vectors;
calculating decision regions around each cluster; and
associating a usage state of the host device with each of the clusters;
performing a monitoring process that includes:
accumulating a second set of feature vectors over a period of time;
determining whether the feature vector or a statistic derived from the second set of feature vectors occupies one or more of the decision regions; and
if the feature vector or statistic occupies one or more of the decision regions, determining a current usage state of the host device based on the decision region or regions occupied by the feature vector or statistic and the usage state associated with the cluster associated with the decision region or regions occupied by the feature vector or statistic.

11. The method of claim 10, wherein the feature vector includes parameters for one or more of: mean, maximum, minimum, median, root mean squared (RMS), fundamental frequency, primary and secondary fundamental frequencies, energy content of primary and secondary fundamental frequencies and harmonics thereof, spectral envelope, period or duty cycle, peak-to-average power of the magnetometer, accelerometer, electric field sensor or microphone samples; light intensity at red, green and blue frequencies from the color sensor; force sensor weight or force measurement; proximity indication from the proximity sensor; or temperature reading from the non-contact temperature sensor.

12. The method of claim 10, wherein the associating is based on ground truth information derived from one or more of: observations of when the host device is actively being used; a video or audio recording of the host device to determine when the host device is actively being used; and optical intensity or color monitoring of one or more of LEDs on the host device through one or more light pipes, one or more external color sensors placed proximate to the LEDs, or one or more battery-powered wireless color sensors placed proximate to the LEDs.

13. The method of claim 10, wherein the learning process further comprises transmitting parameters describing a feature vector definition, the clusters, the decision regions and the associated usage state with each cluster to a network server, and storing the parameters in a database on the network server.

14. The method of claim 10, wherein the monitoring process further comprises receiving a feature vector definition, the decision regions associated each cluster, and the associated usage state with each cluster from a server.

15. The method of claim 10, wherein the monitoring process further comprises: recording times at which there are changes in the current usage state for the host device; computing percentages of time the host device spends in an in-use current usage state; and storing the recorded times or percentages of time in a database on a server.

16. The method of claim 15, wherein the monitoring process further comprises optimizing an overall number or allocation of a plurality of host devices within different parts of a hospital or other facility based on the recorded times or percentages of time for the plurality of host devices.

17. The method of claim 10, wherein the monitoring process further comprises:
calculating outlier statistics on feature vectors that do not occupy any of the decision regions; and
sending an anomaly alert indication if one or more of the outlier statistics exceeds a threshold.

18. The method of claim 10, wherein the monitoring process further comprises mounting multiple UCLS tags to a single host device, and wherein the feature vector comprises parameters derived from the sensor outputs taken from the multiple UCLS tags.

19. The method of claim 10, wherein the monitoring process further comprises varying a measurement interval for electromagnetic activity, temperature, acceleration, sound or ultrasound to conserve battery power on the UCLS tag such that:
when the host device has been previously determined to be in a not-in-use usage state, a relatively short measurement interval is used to determine if there is a minimum threshold of sensor activity, and only when the minimal threshold has been exceeded a longer measurement interval used to verify the host device has transitioned to an in-use operating state; and
when the host device has been previously determined to be in an in-use operating state, a short measurement interval is used to determine if there is a minimum threshold of sensor activity, and only when the minimal threshold has not been exceeded, a longer measurement interval is used to verify the host device has transitioned to a not-in-use operating state.

20. A usage, condition and location system (UCLS), comprising;
one or more UCLS tags, each tag comprising:
a magnetometer or a connection to an external magnetometer configured to provide a measurement of magnetic field activity emanating from electronics contained within a host device to which the tag is attached;
one or more additional sensors or a connection to one or more additional sensors which are external to tag, the one or more additional sensors including:
a contactless temperature sensor configured to provide a temperature measurement of the host device or of a user of the host device;
a force sensor configured to provide a weight measurement associated with the host device;
an accelerometer configured to provide an acceleration measurement of the host device;
an electric field sensor configured to provide a measurement of electric field activity emanating from the electronics contained within the host device;
a microphone configured to provide a sound measurement associated with sounds emitted from the host device;
a color sensor, configured to provide intensity and color measurements of a light source on the host device; and
a proximity sensor, configured to provide a proximity indication of whether a user is on or near the host device;

a processor configured to:
    calculate a feature vector comprising one or more parameters derived from the magnetometer and the one or more additional sensors;
    accumulate feature vectors over a period of time to provide accumulated feature vectors;
    determine whether the feature vector or a statistic derived from the accumulated feature vectors occupies one or more of a set of decision regions stored on the one or more UCLS tags; and
    if the feature vector or statistic occupies one or more of the decision regions, determine a current usage state of the host device based on the decision region or regions occupied by the feature vector or statistic and a learned usage state associated with the decision region or regions occupied by the feature vector or statistic;
a wireless transceiver configured to transmit a data packet that includes information representing the current usage state; and
an energy storage device configured to supply power to the magnetometer, the one or more additional sensors, the processor and the wireless transceiver;
a UCLS server; and
one or more user terminals, wherein:
    the UCLS server determines the location of the one or more UCLS tags using data packets transmitted by the one or more UCLS tags;
    the UCLS server extracts one or more current usage states from the data packets transmitted by the one or more UCLS tags and stores the one or more current usage states in a database; and
    the one or more user terminals retrieve the current usage states from the database via the UCLS server and display the current usage states to one or more users.

21. The system of claim 20, wherein the magnetometer is a single or multi-axis hall-effect sensor, a single or multi-axis e-compass, or an inductive wire loop antenna element.

22. The system of claim 20, wherein the UCLS tag, the external magnetometer, or one of the one or more additional sensors which are external to the tag is configured to be mounted to one of the following positions on the host device: on an enclosure of the host device; on a front or back of a display screen; on an enclosure of the host device proximate to an AC-to-DC converter and/or a DC power supply of the host device; on an enclosure of the host device, proximate to an electric motor; or on or proximate to a light-emitting diode (LED) on the host device.

23. The system of claim 20, wherein the connection to the external magnetometer or the connection to the one or more additional sensors is a wireless connection or wired connection.

24. The UCLS tag of claim 1, wherein the magnetometer is a single or multi-axis hall-effect sensor, a single or multi-axis e-compass, or an inductive wire loop antenna element.

25. The method of claim 10, wherein the magnetometer is a single or multi-axis hall-effect sensor, a single or multi-axis e-compass, or an inductive wire loop antenna element.

* * * * *